US011331498B2

(12) United States Patent
McSpadden et al.

(10) Patent No.: US 11,331,498 B2
(45) Date of Patent: May 17, 2022

(54) METHOD AND SYSTEM TO DETERMINE CAPTURE THRESHOLDS

(71) Applicant: Pacestter, Inc., Sylmar, CA (US)

(72) Inventors: Luke McSpadden, Los Angeles, CA (US); Fujian Qu, San Jose, CA (US); Cyrille S. Casset, Saint Selve (FR); Chunlan Jiang, Xicheng District (CH); Kyungmoo Ryu, Palmdale, CA (US); Caroline D. Jordan, Los Altos Hills, CA (US); Yelena Nabutovsky, Mountain View, CA (US); Nima Badie, Mountain View, CA (US)

(73) Assignee: PACESETTER, INC., Sylmar, CA (US)

( * ) Notice: Subject to any disclaimer, the term of this patent is extended or adjusted under 35 U.S.C. 154(b) by 415 days.

(21) Appl. No.: 16/295,928

(22) Filed: Mar. 7, 2019

(65) Prior Publication Data

US 2019/0201697 A1  Jul. 4, 2019

Related U.S. Application Data

(63) Continuation of application No. 15/067,054, filed on Mar. 10, 2016, now Pat. No. 10,272,249.

(51) Int. Cl.
*A61N 1/37* (2006.01)
*A61N 1/368* (2006.01)
*A61N 1/05* (2006.01)
*A61N 1/02* (2006.01)

(52) U.S. Cl.
CPC ......... *A61N 1/371* (2013.01); *A61N 1/36842* (2017.08); *A61N 1/025* (2013.01); *A61N 1/056* (2013.01); *A61N 1/3712* (2013.01)

(58) Field of Classification Search
CPC .... A61N 1/371; A61N 1/36842; A61N 1/025; A61N 1/056; A61N 1/3712
See application file for complete search history.

(56) References Cited

U.S. PATENT DOCUMENTS

| 2013/0035737 | A1* | 2/2013 | Ryu | A61N 1/36843 607/25 |
| 2015/0134023 | A1* | 5/2015 | McSpadden | A61N 1/36842 607/17 |
| 2017/0216599 | A1* | 8/2017 | Wisnoskey | A61N 1/36542 |

* cited by examiner

*Primary Examiner* — Catherine M Voorhees
*Assistant Examiner* — Roland Dinga
(74) *Attorney, Agent, or Firm* — The Small Patent Law Group LLC; Dean D. Small

(57) ABSTRACT

Computer implemented methods and systems are provided for automatically determining capture thresholds for an implantable medical device equipped for cardiac stimulus pacing using a multi-pole left ventricular (LV) lead. The methods and systems measures a base capture threshold for a base pacing vector utilizing stimulation pulses varied over at least a portion of an outer test range. The base pacing vector is defined by a first LV electrode provided on the LV lead and a second electrode located remote from an LV chamber. The methods and systems designate a secondary pacing vector that includes the first LV electrode and a neighbor LV electrode provided on the LV lead. The methods and systems further define an inner test range having secondary limits based on the base capture threshold, wherein at least one of the limits for the inner test range differs from a corresponding limit for the outer test range. The methods and systems measure a secondary capture threshold associated with the secondary pacing vector utilizing stimulation pulses varied over at least a portion of the inner test range.

9 Claims, 11 Drawing Sheets

METHOD AND SYSTEM TO DETERMINE CAPTURE THRESHOLDS

CROSS REFERENCE TO RELATED APPLICATIONS

This application is a continuation of U.S. patent application Ser. No. 15/067,054, filed Mar. 10, 2016.

BACKGROUND OF THE INVENTION

Embodiments of the present disclosure generally relate to determining capture thresholds, and more particularly to methods and systems to automatically adjust test ranges based on prior measured capture thresholds.

Implantable stimulation devices or cardiac pacemakers are a class of cardiac rhythm management devices that provide electrical stimulation in the form of pacing pulses to selected chambers of the heart. As the term is used herein, a pacemaker is any cardiac rhythm management device with a pacing functionality regardless of any additional functions it may perform, such as cardioversion/defibrillation.

A pacemaker is comprised of two major components, a pulse generator and a lead. The pulse generator generates the pacing stimulation pulses and includes the electronic circuitry and the power cell or battery. The lead, or leads, is implanted within the heart and has electrodes which electrically couples the pacemaker to the desired heart chamber(s). A lead may provide both unipolar and bipolar pacing and/or sensing configurations. In the unipolar configuration, the pacing pulses are generally applied (or responses are sensed) between an electrode carried by the lead and a case of the pulse generator or an electrode of another lead within the heart. In the bipolar configuration, the pacing pulses are applied (or responses are sensed) between a pair of electrodes carried by the same lead. Recently, pacing systems have been introduced that stimulate multiple sites in the same chamber, termed multisite stimulation systems or multi-purpose pacing systems.

When the patient's own intrinsic rhythm fails, pacemakers can deliver pacing pulses to a heart chamber to induce a depolarization of that chamber, which is followed by a mechanical contraction of that chamber. Pacemakers further include sensing circuits that sense cardiac activity for the detection of intrinsic cardiac events such as intrinsic atrial depolarizations (detectable as P waves) and intrinsic ventricular depolarizations (detectable as R waves). By monitoring cardiac activity, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart. This therapy is referred to as cardiac resynchronization therapy (CRT).

Recently, multi-point pacing (MPP) technology has enabled pacing at left ventricular (LV) sites to improve synchrony in cardiac resynchronization therapy (CRT) patients. Improvements in synchrony and improved hemodynamic response have been shown to depend on the MPP configuration. In the past, MPP configurations have been selected based on reducing pacing capture thresholds, avoiding atrial and phrenic nerve capture, and maximizing anatomical distance between LV pacing sites.

Further, quadrupole or multi-electrode LV leads have been found to afford more LV pacing vector options. Different pacing vector options may be chosen in order to avoid high capture thresholds and phrenic nerve stimulation and to select a preferred LV pacing site. Today, various device-based algorithms exist for automatically determining the LV pacing thresholds based on changes in evoked responses. However, existing automatic threshold determining techniques utilize an extended period of time, relative to conventional bipolar leads, when determining capture thresholds for a large number of LV pacing vectors (e.g. 10 or more vectors).

A need remains for improved methods and systems that automatically identify capture thresholds and reduce the time utilized for identifying available LV pacing vectors.

SUMMARY

In accordance with embodiments herein a computer implemented method is provided for automatically determining capture thresholds for an implantable medical device equipped for cardiac stimulus pacing using a multi-pole left ventricular (LV) lead. The method comprises, under control of one or more processors configured with program instructions, measuring a base capture threshold for a base pacing vector utilizing stimulation pulses varied over at least a portion of an outer test range. The base pacing vector is defined by a first LV electrode provided on the LV lead and a second electrode located remote from an LV chamber. The method designates a secondary pacing vector that includes the first LV electrode and a neighbor LV electrode provided on the LV lead. The method further defines an inner test range having secondary limits based on the base capture threshold, wherein at least one of the limits for the inner test range differs from a corresponding limit for the outer test range. The method measures a secondary capture threshold associated with the secondary pacing vector utilizing stimulation pulses varied over at least a portion of the inner test range.

Optionally, the measuring of the base capture threshold includes delivering successive stimulation pulses that have different stimulation amplitudes starting at an upper limit of the outer test range and decreasing by predetermined amounts. The measuring of the secondary capture threshold includes delivering one or more pacing pulses having stimulation amplitudes varying over the inner test range. One or more pacing pulses begins with an initial stimulation amplitude having a voltage that is lower than a voltage of an initial stimulation amplitude associated with the outer test range used to measure the base capture threshold.

Optionally, the measuring of the base and secondary capture thresholds begin at first and second outer voltages corresponding to one of the limits of the outer and inner test ranges, respectively. The first and second outer voltages may differ from one another by an amount based on a correlation map. The second outer voltage is set to equal a predetermined multiple of the first outer voltage or to equal a difference between the first outer voltage and a predetermined offset.

The method further comprises setting the first LV electrode, utilized to define the base and secondary pacing vectors, as a cathode electrode and setting the second electrode and the neighboring LV electrode as anode electrodes. The method may set the base pacing vector to represent a unipolar pacing configuration, such that the base capture threshold represents a unipolar capture threshold, and may set the secondary pacing vector to represent a bipolar pacing configuration, such that the secondary capture threshold represents a bipolar capture threshold.

Optionally, measuring the secondary capture threshold includes defining a select cut off limit for the inner test range and beginning measurements for the secondary capture threshold at the select cut off limit, when loss of capture is detected at the select cut off limit, proceeding to a next pacing vector without determining a capture threshold associated with the secondary capture vector. The measuring, designating and defining operations are repeated for multiple secondary pacing vectors associated with the base pacing vector. The measuring, designating and defining operations are repeated for multiple base pacing vectors, each of which has at least one secondary pacing vector. Optionally, at least one of measuring the base capture threshold or measuring the secondary capture threshold may comprise performing a quick scan such that, when loss of capture is detected, the process proceeds to a next pacing vector.

In accordance with embodiments herein a system is provided for automatically determining capture thresholds for an implantable medical device equipped for cardiac stimulus pacing using a multi-pole left ventricular (LV) lead. The system comprises at least one processor and a memory coupled to the at least one processor, wherein the memory stores program instructions. The program instructions are executable by the at least one processor. The system measures a base capture threshold for a base pacing vector utilizing stimulation pulses varied over at least a portion of an outer test range, the base pacing vector defined by a first LV electrode provided on the LV lead and a secondary electrode located remote from an LV chamber. The system designates a secondary pacing vector that includes the first LV electrode and a neighbor LV electrode provided on the LV lead. The system further comprises a defined inner test range having limits based on the base capture threshold, wherein at least one of the limits for the inner test range differs from a corresponding limit for the outer test range. The system measures a secondary capture threshold associated with the secondary pacing vector utilizing stimulation pulses varied over at least a portion of the inner test range.

Optionally, the system comprises a pulse generator that delivers, in connection with measuring the base capture threshold, successive stimulation pulses that have different stimulation amplitudes starting at an upper limit of the outer test range and decreasing by predetermined amounts. The system further comprises a pulse generator that delivers, in connection with measuring the secondary capture threshold, one or more pacing pulses having stimulation amplitudes that vary over the inner test range.

Optionally, the pulse generator delivers one or more pacing pulses beginning with an initial stimulation amplitude having a voltage that is lower than a voltage of an initial stimulation amplitude associated with the outer test range used to measure the base capture threshold. The pulse generator, in connection with measuring the base and secondary capture thresholds, begins at first and second outer voltages corresponding to one of the limits of the outer and inner test ranges, respectively, the first and second outer voltages differing from one another. Optionally, a correlation map may define a relation between the base capture threshold and at least one outer limit of the Inner test range.

Optionally, the second outer voltage is set to equal a predetermined multiple of the first outer voltage or to equal a difference between the first outer voltage and a predetermined offset. The system may further comprise a pulse generator and a switch, the switch defining the base and secondary pacing vectors by connecting the pulse generator to the first LV electrode in a manner that sets the first LV electrode as a cathode electrode, the switch connecting the second electrode and the neighbor LV electrode as anode electrodes. The system may further comprise a switch that sets the base pacing vector to represent a unipolar pacing configuration and that sets the secondary pacing vector to represent a bipolar pacing configuration.

BRIEF DESCRIPTION OF THE DRAWINGS

FIG. 28 illustrates examples of correlation maps that may be stored in the memory in accordance with embodiments herein.

DETAILED DESCRIPTION

Figure 1:
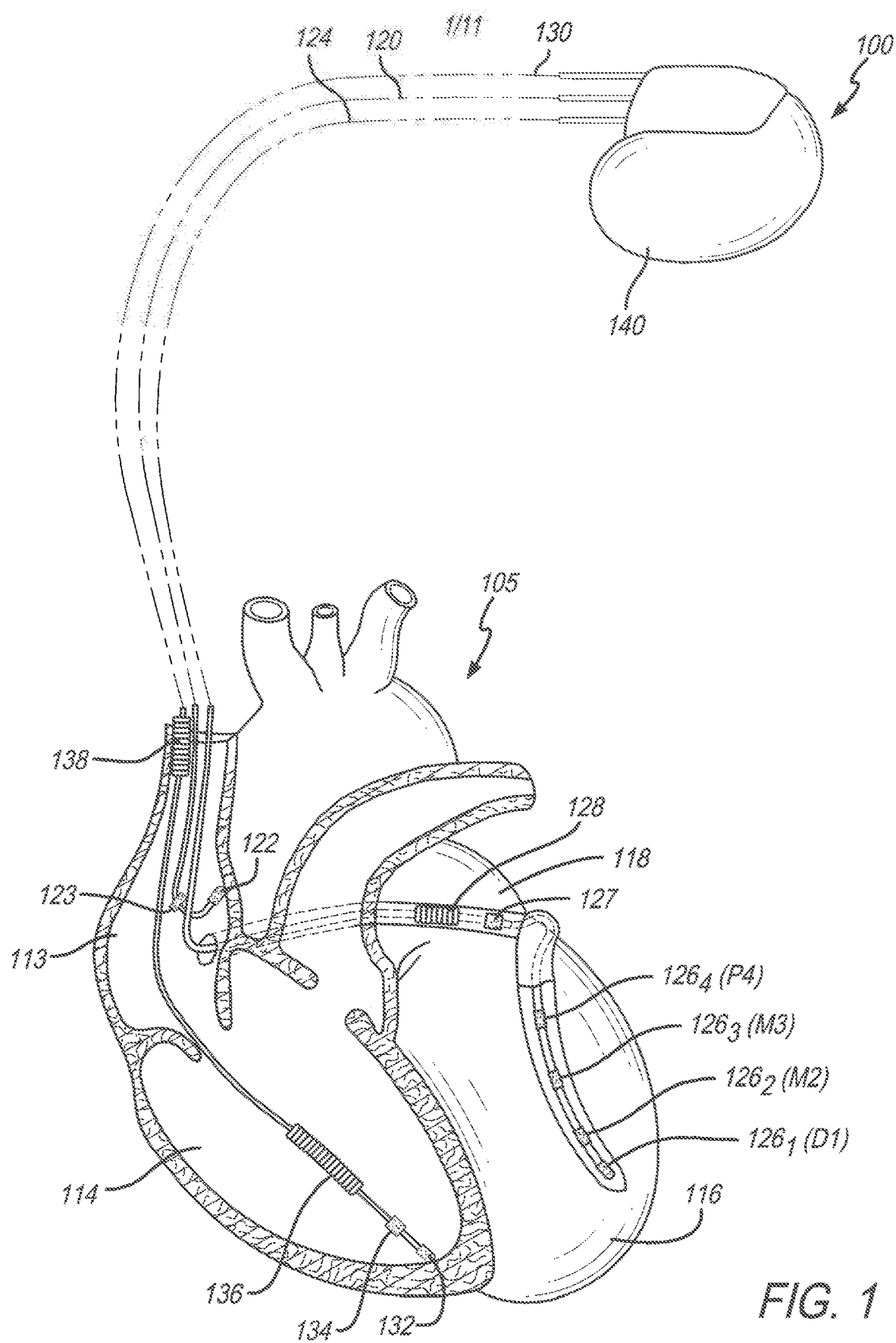
FIG. 1 illustrates an implantable medical device (IMD) in electrical communication with multiple leads implanted into a patient's heart for delivering multi-chamber stimulation and sensing cardiac activity according to an embodiment.

The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like (collectively "processors"). These devices may be off-the-shelf devices that perform the operations described herein from the instructions described above. Additionally or alternatively, one or more of these devices may be hard-wired with logic circuits to perform these operations.

The foregoing summary, as well as the following detailed description of certain embodiments, will be better understood when read in conjunction with the appended drawings. To the extent that the FIGS. illustrate diagrams of the functional blocks of various embodiments, the functional blocks are not necessarily indicative of the division between hardware and circuitry. Thus, for example, one or more of the functional blocks (e.g., processors or memories) may be implemented in a single piece of hardware (e.g., a general purpose signal processor, microcontroller, random access memory, hard disk, and/or the like). Similarly, the programs may be standalone programs, may be incorporated as subroutines in an operating system, may be functions in an installed imaging software package, and the like. Furthermore, to the extent that the FIGS. illustrate flow diagrams of processes of various embodiments, the operations may be described by adding, rearranging, combining, or omitting the illustrated operations without departing from the scope of the processes as described herein. It should be understood that the various embodiments are not limited to the arrangements and instrumentality shown in the drawings.

One or more embodiments generally relate to implantable medical devices and systems such as pacemakers and implantable cardioverter-defibrillators (ICDs). One or more embodiments relate, in particular, to such devices and systems that include a multi-pole LV lead capable of pacing from one or more electrodes along the multi-pole lead, and methods for use therewith. New multipolar left ventricular (LV) leads have been developed for implantable medical devices (IMDs) that include multiple electrodes for placement in the LV chamber. For example, St. Jude Medical, Inc. (headquartered in St. Paul, Minn.) has developed the Quartet™ LV pacing lead, which includes four pacing electrodes on the LV lead.

System Overview

In accordance with embodiments herein, methods and systems utilize information determined utilizing select or base pacing vectors in connection with determining test ranges to search for capture thresholds that may be exhibited by other "secondary" pacing vectors. As noted herein, certain combinations of pacing vectors exhibit relations between capture thresholds. When the capture threshold for one pacing vector is measured, it can be useful in predicting a narrow test range to search for the capture threshold of a related pacing vector. The relations are indicated herein as base and secondary.

In accordance with embodiments herein, methods and systems are provided that utilize a predetermined relation (as maintained in a correlation map) between capture thresholds for different pacing vectors to narrow candidate test ranges (also referred to as secondary or inner test ranges) to utilize when searching for capture thresholds associated with secondary pacing vectors. The limits of the secondary or inner test ranges are determined based on the capture threshold measured for one or more base pacing vectors. The methods and systems measure the capture threshold(s) for one or more base pacing vectors. The measured capture thresholds are applied to a correlation map to obtain limits of the Inner test range to be utilized in connection with measuring the capture thresholds for secondary pacing vectors. The inner test range represents a range over which one or more stimulation parameters are varied while searching for a capture threshold for a particular pacing vector. The inner test range may include a limit for an upper or lower end of the range that corresponds to an upper or lower limit of the base test range used in connection with determining the base capture threshold.

The inner test range is narrower than the original "outer" test range used when searching for the capture threshold of a base pacing vector. The inner test range may fall entirely within the outer test range or may only partially overlap the outer test range.

In accordance with embodiments herein, multiple different base pacing vectors are tested to identify associated base capture thresholds. One or more of the base pacing vectors have correlation maps associated with one or more secondary pacing vectors. The correlation maps enable the methods and systems to identify a narrow inner test range with a subset of test points to be measured in search of the capture threshold for the secondary pacing vector(s).

FIG. 1 illustrates an implantable medical device (IMD) 100 in electrical communication with multiple leads implanted into a patient's heart 105 for delivering multi-chamber stimulation and sensing cardiac activity according to an embodiment. The IMD 100 may be a dual-chamber stimulation device, including a IMD, capable of treating both fast and slow arrhythmias with stimulation therapy, including cardioversion, defibrillation, and pacing stimulation, including CRT. Optionally, the IMD 100 may be configured for single site or multi-site left ventricular (MSLV) pacing, which provides pacing pulses at more than one site within the LV chamber each pacing cycle. The IMD 100 may be referred to herein as IMD 100. To provide atrial chamber pacing stimulation and sensing, IMD 100 is shown in electrical communication with a heart 105 by way of a left atrial (LA) lead 120 having an atrial tip electrode 122 and an atrial ring electrode 123 implanted in the atrial appendage 113. IMD 100 is also in electrical communication with the heart 105 by way of a right ventricular (RV) lead 130 having, in this embodiment, a ventricular tip electrode 132, an RV ring electrode 134, an RV coil electrode 136, and a superior vena cava (SVC) coil electrode 138. The RV lead 130 is transvenously inserted into the heart 105 so as to place the RV coil electrode 136 in the RV apex, and the SVC coil electrode 138 in the superior vena cava. Accordingly, the RV lead 130 is capable of receiving cardiac signals and delivering stimulation in the form of pacing and shock therapy to the right ventricle 114 (also referred to as the RV chamber).

To sense left atrial and ventricular cardiac signals and to provide left ventricle 116 (e.g., left chamber) pacing therapy, IMD 100 is coupled to a multi-pole LV lead 124 designed for placement in various locations such as the "CS region", the epicardial space, etc. As used herein, the phrase "CS region" refers to the venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus. In an embodiment, an LV lead 124 is designed to receive atrial and ventricular cardiac signals and to deliver left ventricular pacing therapy using a set of multiple LV electrodes 126 that includes electrodes $126_1$, $126_2$, $126_3$, and $126_4$ (thereby providing a multipolar or multi-pole lead). The LV lead 124 also may deliver left atrial pacing therapy using at least an LA ring electrode 127 and shocking therapy using at least an LA coil electrode 128. In alternate embodiments, the LV lead 124 includes the LV electrodes $126_1$, $126_2$, $126_3$, and $126_4$, but does not include the LA electrodes 127 and 128. The LV lead 124 may be, for example, the Quartet™ LV pacing lead developed by St. Jude Medical Inc. (headquartered in St. Paul, Minn.), which includes four pacing electrodes on the LV lead. Although three leads 120, 124, and 130 are shown in FIG. 1, fewer or additional leads with various numbers of pacing, sensing, and/or shocking electrodes may optionally be used. For example, the LV lead 124 may have more or less than four LV electrodes 126.

When selecting a target venous branch for the LV lead 124, several factors may be taken into account. For example, it may be desirable to maximize the LV mass that may be captured by the LV lead 124. Accordingly, to maximize LV mass exposure, certain venous branches may be preferred for positioning the LV lead 124. Further, a diameter and trajectory of the venous branch is also considered to ensure that the venous branch will support chronic stability of an LV lead 124. Passive fixation of the LV lead 124 may be established through the anatomy of the host venous branch which causes the LV lead 124 to extend the distal portion thereof in a manner that differs from the LV lead's preformed shape. Optionally, additional factors to be considered when placing the LV lead 124 may include reducing myocardial capture thresholds, avoiding atrial and phrenic nerve stimulation and the like. After the LV lead 124 is positioned, the LV pacing vectors may be selected.

The LV electrode $126_1$ (also referred to as P4) is shown as being the most "distal" LV electrode with reference to how far the electrode is from the left atrium 118. The LV electrode $126_4$ (also referred to as D1) is shown as being the most "proximal" LV electrode 126 to the left atrium 118. The LV electrodes $126_2$ and $126_3$ are shown as being "middle" LV electrodes (also referred to as M3 and M2), between the distal and proximal LV electrodes $125_1$ and $126_4$, respectively. Accordingly, so as to more aptly describe their relative locations, the LV electrodes $126_1$, $126_2$, $126_3$, and $126_4$ may be referred to respectively as electrodes D1, M2, M3, and P4 (where "D" stands for "distal", "M" stands for "middle", and "P" stands from "proximal", and the numbers are arranged from most distal to most proximal, as shown in FIG. 1). Optionally, more or fewer LV electrodes may be provided on the lead 124 than the four LV electrodes D1, M2, M3, and P4.

The LV electrodes 126 are configured such that each electrode may be utilized to deliver pacing pulses and/or sense pacing pulses (e.g., monitor the response of the LV tissue to a pacing pulse). In a pacing vector or a sensing vector, each LV electrode 126 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 105 or located externally to the heart 105 (e.g., on a housing/case device 140). For example, the housing/case 140 may be referred to as the CAN 140 and function as an anode in unipolar pacing and/or sensing vectors. The RV coil 136 may also function as an anode in unipolar pacing and/or sensing vectors. The LV electrodes 126 may be used to provide various different vectors. Some of the vectors are intraventricular LV vectors (e.g., vectors between two of the LV electrodes 126), while other vectors are interventricular vectors (e.g. vectors between an LV electrode 126 and the RV coil 136 or another electrode remote from the left ventricle 116). Below is a list of exemplary bipolar sensing vectors with LV cathodes that may be used for sensing using the LV electrodes D1, M2, M3, and P4 and the RV coil 136. In the following list, the electrode to the left of the arrow is assumed to be the cathode, and the electrode to the right of the arrow is assumed to be the anode.

D1→RV coil
M2→RV coil
M3→RV coil
P4→RV coil
D1→M2
D1→P4
M2→P4
M3→M2
M3→P4
P4→M2

It is recognized that various other types of leads and IMDs may be used with various other types of electrodes and combinations of electrodes. The foregoing electrode types/combinations are provided as non-limiting examples. Further, it is recognized that utilizing an RV coil electrode as an anode is merely one example. Various other electrodes may be configured as the anode electrode. Below is a list of exemplary bipolar pacing vectors with LV cathodes that may be used for pacing using the LV electrodes D1, M2, M3, and P4 and the RV coil 136. In the following list, the electrodes to the left of the arrow are assumed to be cathodes, and the electrode to the right of the arrow is assumed to be the anode.

D1→RV coil (or CAN)+M2→RV coil (or CAN)
M2→RV coil (or CAN)+M3→RV coil (or CAN)
M3→RV coil (or CAN)+M4→coil (or CAN)
M2→RV coil (or CAN)+M3→RV coil (or CAN)+P4→RV coil (or CAN)
D1→RV coil (or CAN)+M2→RV coil (or CAN)+M3→RV coil (or CAN)

It is noted that the preceding list is only a subset of the available pacing and sensing vectors for use with the IMD 100. Further, when delivering a series of pacing pulses, one of the above LVEC pacing vectors is used for at least the first pacing pulse in the series. Other pacing vectors may be used for subsequent pulses in the series of pacing pulses. Furthermore, additional pacing pulses may be generated in other chambers of the heart, such as the right ventricle.

Figure 2A:
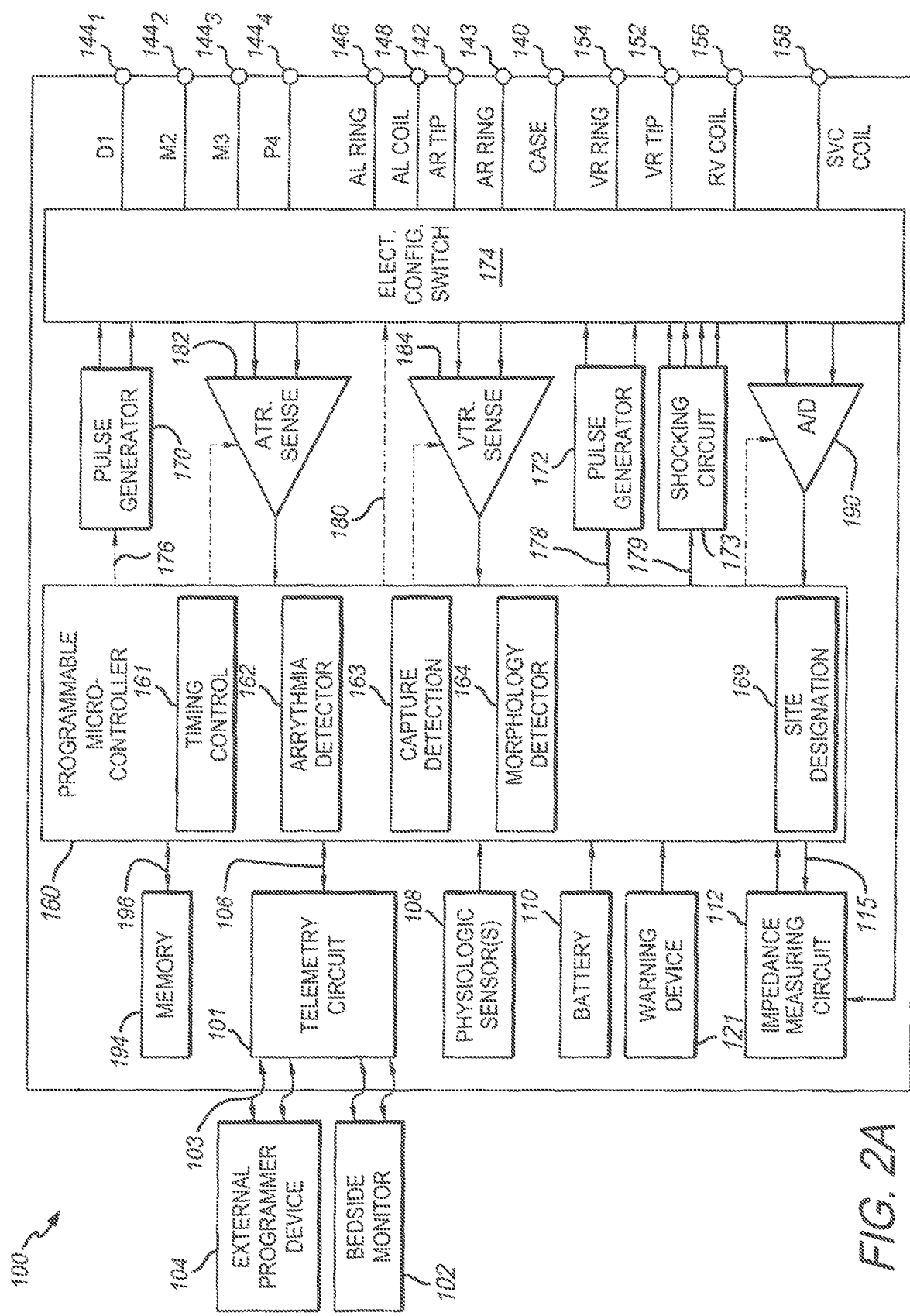
FIG. 2A illustrates a simplified block diagram of internal components of the IMD (e.g., IMD) according to an embodiment.

FIG. 2A illustrates a simplified block diagram of internal components of the IMD 100 (e.g., IMD) according to an embodiment. While a particular IMD 100 is shown, it is for illustration purposes only. One of skill in the art could readily duplicate, eliminate, or disable the appropriate circuitry in any desired combination to provide a device capable of treating the appropriate chamber(s) with cardioversion, defibrillation, and pacing stimulation. The housing/CAN 140 for IMD 100, shown schematically in FIG. 2A may be programmably selected to act as the anode for at least some unipolar modes. The CAN 140 may further be used as a return electrode alone or in combination with one or more of the coil electrodes 128, 136, and 138 (all shown in FIG. 1) for shocking purposes.

The IMD 100 further includes a connector (not shown) having a plurality of terminals, 142, 143, 144$_1$-144$_4$, 146, 148, 152, 154, 156, and 158 (shown schematically and, for convenience, with the names of the electrodes to which they are connected). As such, to achieve right atrial (RA) sensing and pacing, the connector includes at least an RA tip terminal (AR TIP) 142 adapted for connection to the atrial tip electrode 122 (shown in FIG. 1) and an RA ring (AR RING) electrode 143 adapted for connection to the RA ring electrode 123 (shown in FIG. 1). To achieve left chamber sensing, pacing, and shocking, the connector includes an LV tip terminal 144$_1$ adapted for connection to the D1 electrode and additional LV electrode terminals 144$_2$, 144$_3$, and 144$_4$ adapted for connection to the M2, M3, and P4 electrodes, respectively, of the Quadripolar LV lead 124 (shown in FIG. 1). The connector also includes an LA ring terminal ($A_L$ RING) 146 and an LA shocking terminal ($A_L$ COIL) 148, which are adapted for connection to the LA ring electrode 127 (shown in FIG. 1) and the LA coil electrode 128 (shown in FIG. 1), respectively. To support right chamber sensing, pacing, and shocking, the connector further includes an RV tip terminal ($V_R$ TIP) 152, an RV ring terminal ($V_R$ RING) 154, an RV coil terminal (RV COIL) 156, and an SVC coil terminal (SVC COIL) 158, which are adapted for connection to the RV tip electrode 132, the RV ring electrode 134, the RV coil electrode 136, and the SVC coil electrode 138 (all four electrodes shown in FIG. 1), respectively.

At the core of the IMD 100 is a programmable microcontroller 160, which controls the various modes of stimulation therapy. The microcontroller 160 (also referred to herein as a control unit or controller) includes a microprocessor or equivalent control circuitry, designed specifically for controlling the delivery of stimulation therapy. The microcontroller 160 may further include RAM or ROM memory, logic and timing circuitry, state machine circuitry, and/or I/O circuitry. The microcontroller 160 includes the ability to process or monitor input signals (data) as controlled by a program code stored in a designated block of memory. The details of the design and operation of the microcontroller 160 are not critical to the invention. Rather, any suitable microcontroller 160 may be used that carries out the functions described herein. Among other things, the microcontroller 160 receives, processes, and manages storage of digitized cardiac data sets from the various sensors and electrodes.

A pulse generator 170 and a pulse generator 172 are configured to generate and deliver a pacing pulse from at least one RV or RA pacing site, such as at one or more pacing sites along the RA lead 120, the RV lead 130, and/or the LV lead 124 (all three leads shown in FIG. 1). For example, the pulse generator 170 generates pulses for delivery by the RA lead 120 and/or RV lead 130, while the pulse generator 172 generates pulses for delivery by the LV lead 124. The pacing pulses are routed from the pulse generators 170, 172 to selected electrodes within the leads 120, 124, 130 through an electrode configuration switch 174. It is understood that in order to provide stimulation therapy in each of the four chambers of the heart, the pulse generators 170 and 172, may include dedicated, independent pulse generators, multiplexed pulse generators, or shared pulse generators. The pulse generators 170, 172 are controlled by the microcontroller 160 via appropriate control signals 176, 178, respectively, to trigger or inhibit the stimulation pulses, including the timing and output of the pulses.

The pulse generators 170, 172 deliver, in connection with measuring the base capture threshold, successive stimulation pulses that have different stimulation amplitudes starting at an upper limit of the outer test range and decreasing by predetermined amounts. The pulse generators 170, 172 deliver, in connection with measuring the secondary capture threshold, one or more pacing pulses having stimulation amplitudes that vary over the inner test range.

Optionally, the pulse generators 170, 172 deliver one or more pacing pulses beginning with an initial stimulation amplitude having a voltage that is lower than a voltage of an initial stimulation amplitude associated with the outer test range used to measure the base capture threshold. The pulse generators 170, 172, in connection with measuring the base and secondary capture thresholds, begin at first and second outer voltages corresponding to one of the limits of the outer and inner test ranges, respectively, the first and second outer voltages differing from one another.

The electrode configuration switch 174 may include a plurality of switches for connecting the desired electrodes to the appropriate I/O circuits, thereby providing complete electrode programmability. Accordingly, the switch 174, in response to a control signal 180 from the microcontroller 160, controls the polarity of the stimulation pulses (e.g., unipolar, bipolar, etc.) by selectively actuating the appropriate combination of switches (not shown) as is known in the art. The switch 174 also switches among the various LV electrodes 126 to select the channels (e.g., vectors) to deliver and/or sense one or more of the pacing pulses. As explained herein, the switch 174 couples multiple LV electrode terminals $144_1$-$144_4$ correspond to cathodes when connected to the pulse generator 172.

Atrial sensors or sensing circuits 182 and ventricular sensors or sensing circuits 184 may also be selectively coupled to the RA lead 120, the LV lead 124, and/or the RV lead 130 (all three leads shown in FIG. 1) through the switch 174. The atrial and ventricular sensors 182 and 184 have the ability to detect the presence of cardiac activity in each of the four chambers of the heart 105 (shown in FIG. 1). For example, the ventricular sensor 184 is configured to sense LV activation events at multiple LV sensing sites, where the activation events are generated in response to a pacing pulse or an intrinsic event. In an embodiment, the ventricular sensor 184 senses along at least four sensing vectors, each sensing vector utilizing a sensing electrode in the left ventricle.

The atrial sensing circuits 182 and ventricular sensing circuits 184 may include dedicated sense amplifiers, multiplexed amplifiers, or shared amplifiers. The switch 174 determines the "sensing polarity" or sensing vector of the cardiac signal by selectively opening and/or closing the appropriate switches, as is known in the art. In this way, a clinician may program the sensing polarity independent of the stimulation polarity. The outputs of the atrial and ventricular sensing circuits 182 and 184 are connected to the microcontroller 160. The outputs, in turn, are able to trigger or inhibit the atrial and ventricular pulse generators 170 and 172, respectively, in a demand fashion in response to the absence or presence of cardiac activity in the appropriate chambers of the heart 105.

Cardiac signals are also applied to the inputs of an analog-to-digital (A/D) data acquisition system 190. The A/D data acquisition system 190 is configured to acquire intracardiac electrogram (IEGM) signals, convert the raw analog data into a digital signal, and store the digital signals for later processing and/or telemetric transmission. The telemetric transmission may be to an external programmer 104, a bedside monitor, and/or a personal advisory module (PAM) 102. The data acquisition system 190 may be operatively coupled to the RA lead 120, the LV lead 124, and the RV lead 130 (all three leads shown in FIG. 1) through the switch 174 to sample cardiac signals across any pair of desired electrodes.

The microcontroller 160 includes timing control module 161 to control the timing of the stimulation pacing pulses, including, but not limited to, pacing rate, atrio-ventricular delay, interatrial conduction delay, interventricular conduction delay, and/or intraventricular delay. The timing control module 161 can also keep track of the timing of refractory periods, blanking intervals, noise detection windows, evoked response detection windows, alert intervals, marker channel timing, etc., which is known in the art.

The microcontroller 160 further includes an arrhythmia detector 162 for operating the system 100 as an implantable cardioverter/defibrillator device. The detector 162 determines desirable times to administer various therapies. For example, the detector 162 may detect the occurrence of an arrhythmia and automatically control the application of an appropriate electrical shock therapy to the heart aimed at terminating the detected arrhythmia. To this end, the microcontroller 160 further controls a shocking circuit 173 by way of a control signal 179. The shocking circuit 173 generates shocking pulses that are applied to the heart of the patient through at least two shocking electrodes. The shocking pulses may be selected from the LA coil electrode 128, the RV coil electrode 136, and/or the SVC coil electrode 138 (all three electrodes shown in FIG. 1). The CAN 140 may act as an active electrode in combination with the RV coil electrode 136, or as part of a split electrical vector using the SVC coil electrode 138 or the LA coil electrode 128 (e.g., with the RV coil electrode 136 as a common electrode).

The microcontroller 160 may additionally include a morphology detector 164. The arrhythmia detector 162 and/or morphology detector 164 may be implemented in hardware as part of the microcontroller 160, or as software/firmware instructions programmed into the system 100 and executed on the microcontroller 160 during certain modes of operation.

The microcontroller 160 controls the actual delivery of CRT pacing pulses to synchronize the contractions of the right and left ventricles. The microcontroller 160 controls the number, timing, and output of the CRT pacing pulses delivered during each cardiac cycle, as well as over which pacing vectors the pacing pulses are to be delivered. The microcontroller 160 also selects the sensing channels over which the responses to the pulses are detected. The sensing channels or vectors are associated with corresponding pacing vectors. Immediately after pacing, the electrodes at the LV sensing sites that define the selected sensing channels monitor the LV tissue for a sensed activation event.

The microcontroller 160 further includes a capture detection module 163. The capture detection module 163 may aid in acquisition, analysis, etc., of data streams relating to evoked responses sensed at various LV sensing sites along corresponding sensing channels. In particular, the capture detection module 163 may act to distinguish capture versus non-capture versus undesired fusion of pacing pulses delivered along corresponding pacing vectors. The capture detection module 163 determines capture thresholds of individual pacing vectors associated with one or more LV sensing sites. The microcontroller 160 and capture detection module 163 operate as described herein to narrow test ranges used when search for capture thresholds for secondary pacing vectors based on previously determined capture thresholds for other pacing vectors. The operation of the microcontroller 160 and capture detection module 163, as used in connection with determining capture thresholds, as described in more detail below in connection with FIGS. 4A-4C. The capture threshold may be used by the microcontroller 160 to determine the LVEC pacing site and the pacing vector at the LVEC pacing site along which to deliver LV pacing pulses, as described further below.

The pulse generator 170, 172 deliver a pacing sequence from the LV electrode combination designated for the first LVEC pacing site. The pulse generator 170, 172 deliver a first LV pacing pulse in the pacing sequence from the LV electrode combination. As noted herein, the LV electrode combination includes an adjacent pair of LV electrodes. The pulse generator 170, 172 is coupled to the switch 174 that sets the adjacent pair of LV electrodes as cathodes when delivering the LV pacing pulse. Optionally, the pulse generator 170, 172 and switch 174, controlled by the site designation module 169 designate adjacent at least first and second LV electrodes as cathodes to simultaneously deliver at least a first pacing pulse.

Depending upon the implementation, the aforementioned components of the microcontroller 160 may be implemented in hardware as part of the microcontroller 160, or as software/firmware instructions programmed into the device and executed on the microcontroller 160 during certain modes of operation. In addition, the modules may be separate software modules or combined to permit a single module to perform multiple functions. In addition, although shown as being components of the microcontroller 160, some or all of the components/modules described above may be implemented separately from the microcontroller 160 using application specific integrated circuits (ASICs) or the like.

The microcontroller 160 is further coupled to a memory 194 by a suitable data/address bus 196. The programmable operating parameters used by the microcontroller 160 are stored in the memory 194 and modified, as required, in order to customize the operation of IMD 100 to suit the needs of a particular patient. Such operating parameters define, for example, the amplitude or magnitude of the generated pacing pulses, wave shape, pulse duration, and/or vector (e.g., including electrode polarity) for the pacing pulses. Other pacing parameters may include base rate, rest rate, and/or circadian base rate. The memory 194 also may be utilized to store, at least temporarily, determined characteristics about one or more pacing vectors, such as capture thresholds and the presence or absence of phrenic nerve stimulation (PNS), which is a potential side effect. The memory 194 stores one or more correlation maps that are used to narrow test ranges when searching for capture thresholds.

Figure 2B:
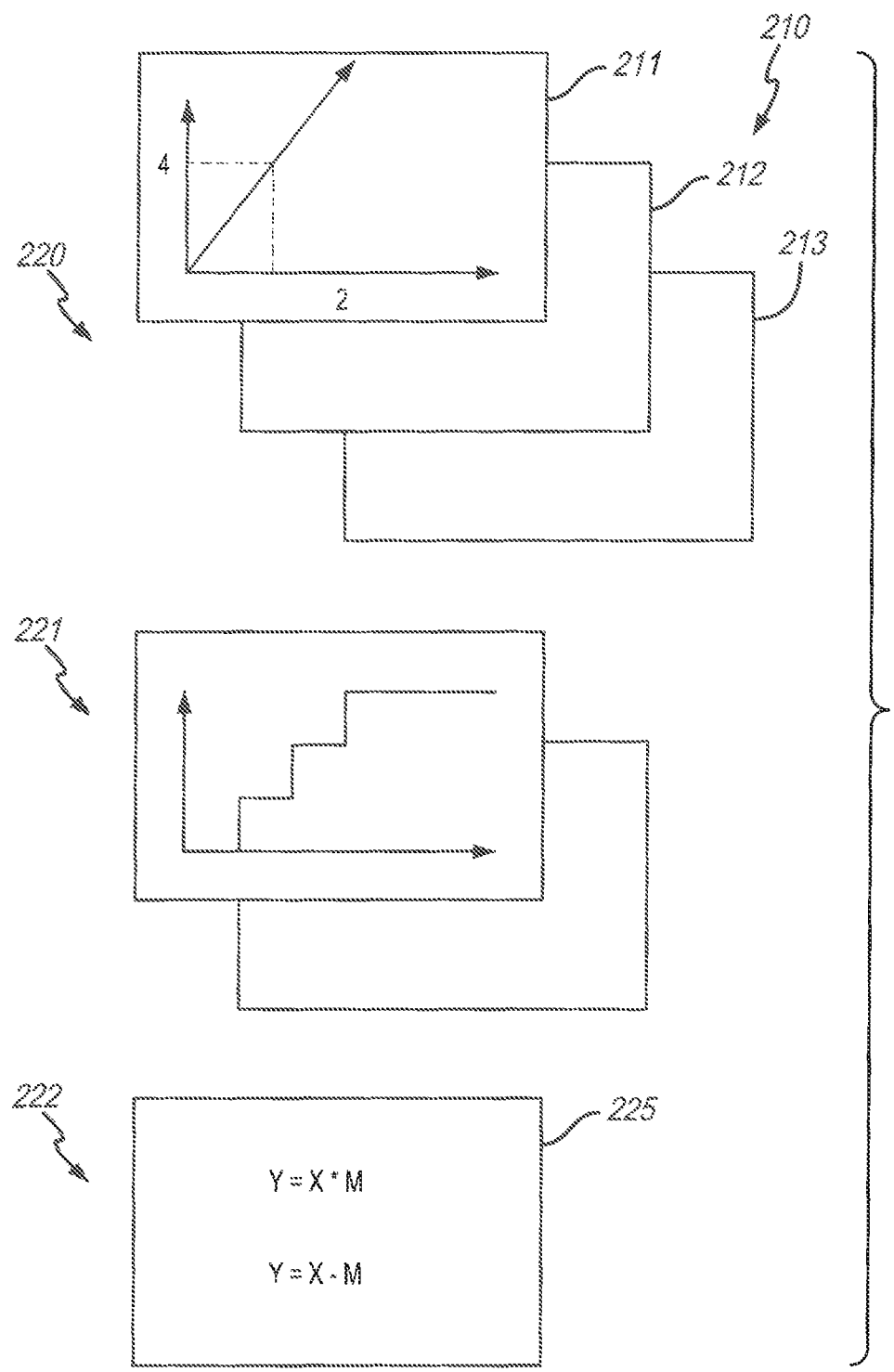

FIG. 2B illustrates examples of correlation maps that may be stored in the memory 194. The correlation maps 210 may include separate sets 220-222 of maps, where each set 220-222 is related to a particular combination of a base pacing vector and one or more secondary pacing vectors that are known to have a relation with the base pacing vector. For example, set 220 includes maps 211-213, each of which relates to a different combination of a common base pacing vector and different secondary pacing vectors. For example, the map 211 may correspond to the D1-RV coil base pacing vector and the D1-M2 secondary pacing vector, while map 212 corresponds to the D1-RV coil base pacing vector and D1-P4 secondary pacing vector. The set 221 may correspond to a different base pacing vector (e.g. M3-RV coil), while the set 222 corresponds to get a different base pacing vector.

FIG. 2B further illustrates examples of correlation functions. For example, the map 211 illustrates a graph plotting a linear function where the capture threshold associated with the base pacing vectors plotted along the horizontal axis, while an upper limit of an inner test range associated with the secondary pacing vector is plotted along the vertical axis. In the example of FIG. 2B, when the capture threshold of the base pacing vector is identified to be 2 V, the upper limit of the inner test range associated with the secondary pacing vector may be set to 4 V. In the foregoing example, the secondary pacing vector would be tested for capture thresholds beginning at 4 V and then decreasing the past value by a predetermined amount during each successive stimulation pulse. The maps 212 and 213 may Include the same linear correlation function or different correlation functions.

The set 221 illustrates an example of an alternative type of correlation function that may be used to define the relation between the capture threshold for the base pacing vector and the upper limit of the inner test range for the secondary pacing vector. For example, the correlation function may represent a stepped function where the upper limit of the inner test range is progressively increased by stepped values as the capture threshold of the base pacing vector increases.

As yet another example, the map 225 illustrates examples of simple mathematical formula that may be used to define the relation. For example, the formula may be one or more of $Y=X*M$ and/or $Y=X+M$, where the X variable corresponds to the capture threshold of the base pacing vector and be Y variable corresponds to the upper limit of the inner test range and the constant M corresponds to a predetermined offset programmed by a physician or automatically set based on past experiences. The correlation maps may be defined in various manners. For example, physician may program the correlation map. Alternatively, the system may automatically generate correlation maps based upon prior patients or based upon past experience with an individual patient. As another example, correlation maps may be preprogrammed based on historic patient the data for a large population of patients. As one example, patient data related to a large population of patients were analyzed (as described below in more detail in connection with FIG. 3A-3C) to identify relationships between capture thresholds associated with particular combinations of pacing vectors. The relationships may then be used to define correlation maps to be programmed into the memory 194.

Returning to FIG. 2A, optionally, the operating parameters of the implantable IMD 100 may be non-invasively programmed into the memory 194 through a telemetry circuit 101 in telemetric communication with an external programmer device 104 or a bedside monitor 102, such as a programmer, trans-telephonic transceiver, or a diagnostic system analyzer. The telemetry circuit 101 is activated by the microcontroller 160 through a control signal 106. The telemetry circuit 101 may allow IEGMs and status information relating to the operation of IMD 100 (contained in the microcontroller 160 or the memory 194) to be sent to the external device 102, and vice-versa, through an established communication link 103. An internal warning device 121 may be provided for generating perceptible warning signals to a patient and/or caregiver via vibration, voltage, or other methods.

IMD 100 further includes an accelerometer or other physiologic sensor 108. The physiologic sensor 108 is commonly referred to as a "rate-responsive" sensor because it may be used to adjust the pacing stimulation rate according to the exercise state (e.g., heart rate) of the patient. However, the physiological sensor 108 may further be used to detect changes in cardiac output, changes in the physiological condition of the heart, and/or diurnal changes in activity (e.g., detecting sleep and wake states and arousal from sleep). Accordingly, the microcontroller 160 may respond to such changes by adjusting the various pacing parameters (such as rate, interatrial delay, interventricular delay, etc.) at which the atrial and ventricular pulse generators 170 and 172 generate stimulation pulses. While shown as being included within IMD 100, it is to be understood that the physiologic sensor 108 may also be external to the IMD 100. Optionally, the physiologic sensor 108 may still be implanted within or carried by the patient. A common type of rate responsive sensor 108 is an activity sensor incorporating an accelerometer or a piezoelectric crystal, which is mounted within the housing/case 140 of IMD 100. Other types of physiologic sensors 108 are also known, such as sensors that sense the oxygen content of blood, respiration rate and/or minute ventilation, pH of blood, ventricular gradient, stroke volume, cardiac output, contractility, and the like.

The IMD 100 additionally includes a battery 110, which provides operating power to all of the circuits shown in FIG. 2. The makeup of the battery 110 may vary depending on the capabilities of IMD 100. If the system only provides low voltage therapy (e.g., for repetitive pacing pulses), a lithium iodine or lithium copper fluoride cell may be utilized. For a IMD that employs shocking therapy, the battery may be configured to be capable of operating at low current drains for long periods and then providing high-current pulses (for capacitor charging) when the patient requires a shock pulse. The battery 110 may also be configured to have a predictable discharge characteristic so that elective replacement time can be detected.

As further shown in FIG. 2A, the IMD 100 has an impedance measuring circuit 112, which is enabled by the microcontroller 160 via a control signal 115. Uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 112 is coupled to the switch 174 so that any desired electrode may be used.

The above described implantable medical device 100 was described as an exemplary IMD. One of ordinary skill in the art would understand that one or more embodiments herein may be used with alternative types of implantable devices. Accordingly, embodiments should not be limited to using only the above described device 100.

Figure 3A:
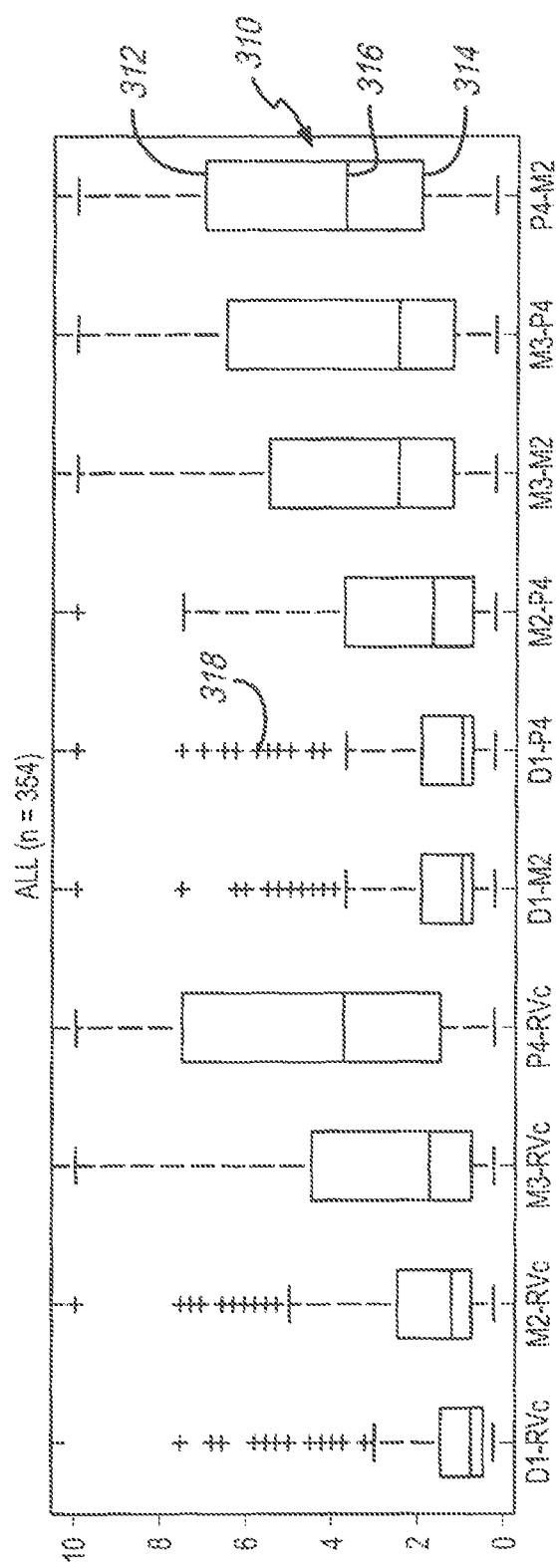
FIG. 3A illustrates LV capture thresholds collected for patients utilizing a quadrupole LV lead and a lead having an RV coil electrode in the right ventricle in accordance with embodiments herein.
Figure 3B:
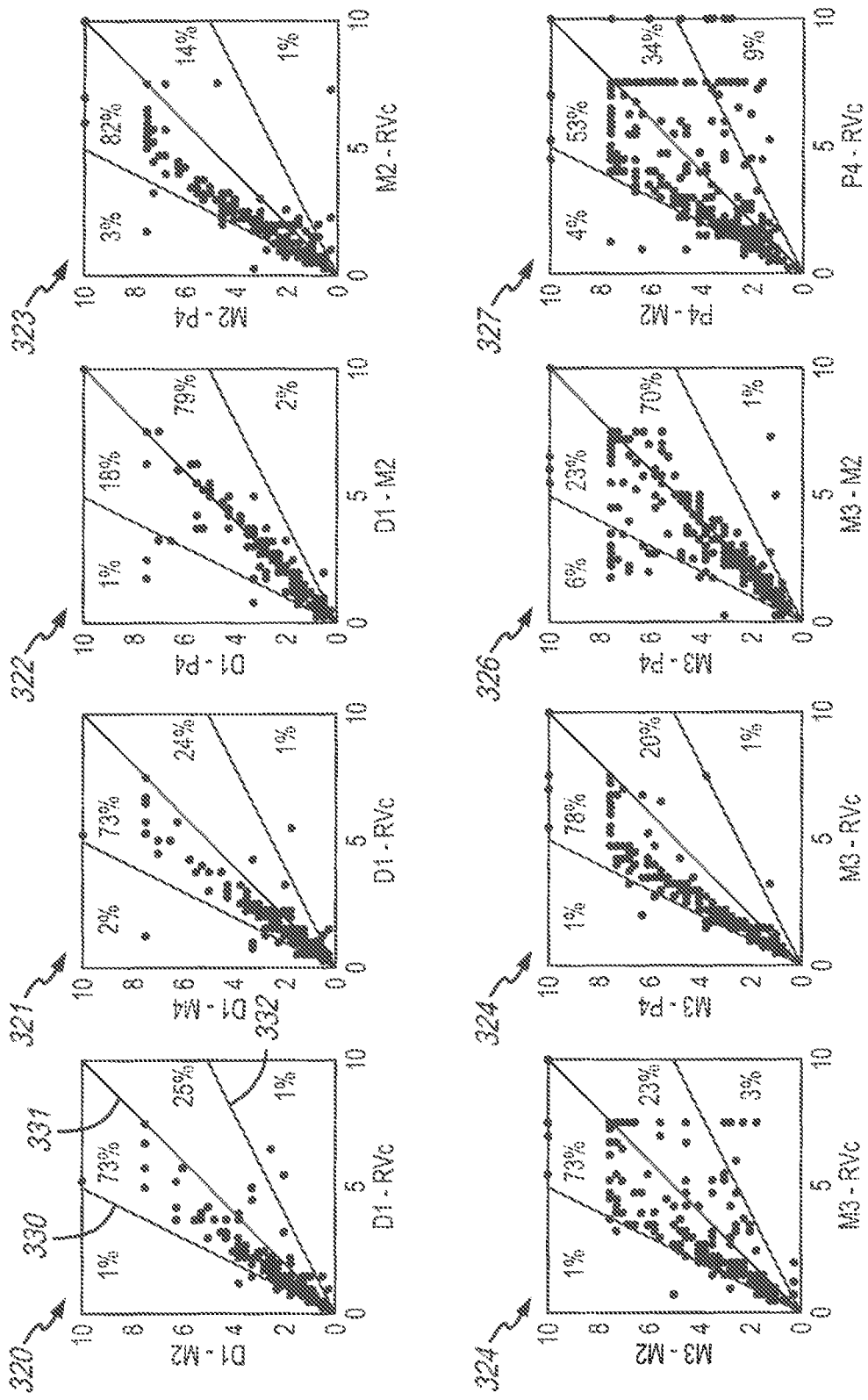
FIG. 3B illustrates a collection of correlation plots that map capture thresholds associated with different combinations of pacing vectors relative to one another in accordance with embodiments herein.
Figure 3C:
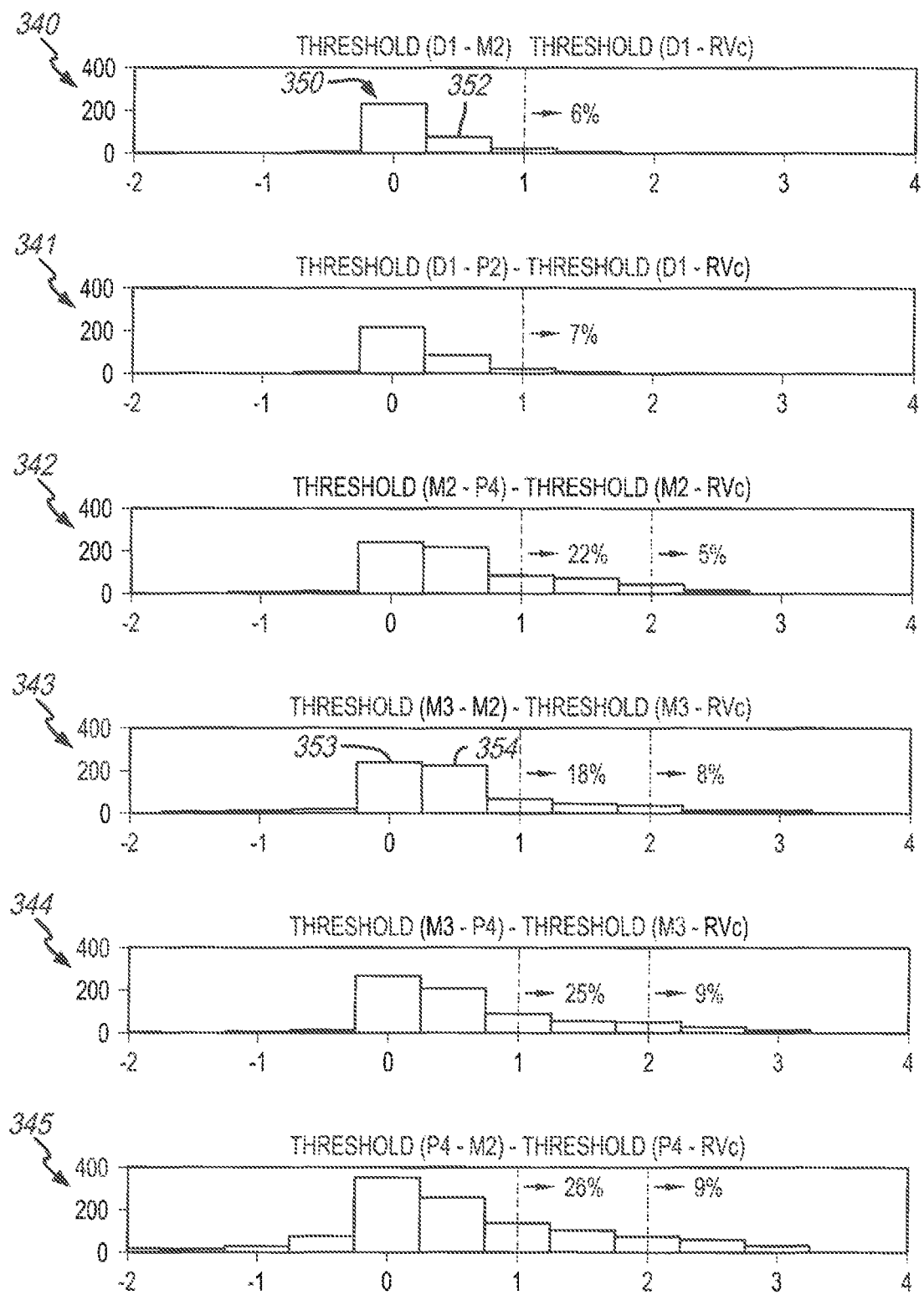
FIG. 3C illustrates a series of histograms plotting differences between capture thresholds for the same patient data used to derive the graphs and plots in FIGS. 3A and 3B in accordance with embodiments herein.

FIGS. 3A-3C illustrate data collected from studies using Quartet Quadripolar LV leads in accordance with embodiments herein. The data in FIGS. 3A-3C generally indicate that capture thresholds for a given cathode is often lowest when in the unipolar configuration (e.g., when an RV coil electrode is used as an anode). Capture thresholds for bipolar vectors are generally higher than the capture thresholds for a corresponding unipolar vector (e.g. two times higher).

FIG. 3A illustrates LV capture thresholds collected for 354 patients utilizing a quadrupole LV lead and a lead having an RV coil electrode in the right ventricle. When measuring the capture thresholds, various combinations of electrodes were utilized, as denoted along the horizontal axis. In particular, the electric combinations included the D1-RV coil electrode pair, M2-RV coil electrode pair, M3-RV coil electrode pair, P4-RV coil electrode pair, D1-M2 electrode pair, D1-P4 electrode pair, M2-P4 electrode pair, M3-M2 electrode pair, M3-P4 electrode pair and the P4-M2 electrode pair. The vertical axis represents the voltage level associated with the capture threshold for each patient. The data is organized in a box plot format where the data associated with each electrode pair is arranged in each bar 310, where the upper level 312 represents the third quartile (75%) of the data, while the lower level 314 represents the first quartile (25%). The intermediate line 316 represents the median for the capture thresholds collected in connection with the pacing vector defined by the corresponding electrode pair. The additional markers 318 represent data outliers that are lower than the 1.5 interquartile range (IQR) of the first quartile, and higher than the 1.5 IRQ of the third quartile.

Upon inspecting the data in FIG. 3A, one characteristic that becomes apparent is that pacing vectors that utilize a unipolar configuration, for example when the RV coil represents the anode, exhibit lower capture thresholds, as compared to pacing vectors that utilize a bipolar configuration, in which the anode corresponds to an LV electrode. For example, the first and third quartiles of capture thresholds associated with the D1-RV coil electrode combination fall within a very small range between 0.5 V and less than 2 V. Further, similarities in the first and third quartiles of capture thresholds are clear when comparing the D1-RV coil electrode combination with the D1-M2 and D1-P4 electrode combinations, all of which use a common D1 electrode as the cathode. As another example, the first and third quartiles of the capture thresholds are similar for the M2-RV coil electrode combination and M2-P4 electrode combination, both of which use a common M2 electrode as the cathode. As another example, the first and third quartiles of the capture thresholds are similar for the M3-RV coil electrode combination and the M3-M2 electrode combination, both of which use the M3 electrode as the cathode.

In FIG. 3B, a collection of correlation plots are illustrated that map capture thresholds associated with different pacing vectors with the same cathode electrode in accordance with embodiments herein. In the plots 320-327, the horizontal axis corresponds to the capture thresholds measured in connection with one pacing vector, while the vertical axis corresponds to the capture thresholds measured in connection with another "related" pacing vector.

The pacing vectors along the horizontal axis may generally be referred to as "base" pacing vectors while the pacing vectors along the vertical axis may be referred to as "secondary". The terms base and secondary are used to indicate a relation between the pacing vectors. For example, when the capture threshold for a base pacing vector is measured, the information can be used to narrow the test range when searching for the capture threshold of the secondary pacing vector.

A pacing vector may represent a secondary basing vector (e.g., plot 320 D1-M2) relative to one pacing vector (e.g., D1-RVc). The same pacing vector may represent a base pacing vector (e.g., plot 322, D1-M2) relative to another pacing vector (D1-P4).

Each data point in an individual plots 320-327 corresponds to a pair of capture thresholds exhibited by an individual patient. The plots 320-327 illustrates capture thresholds for combinations of pacing vectors that utilize at least one LV electrode as a common cathode. For example, the data in plot 320 shows a relation between capture thresholds (between zero and 10 V) associated with the pacing vector D1-RV coil (along the horizontal axis) and the capture thresholds associated with pacing vector D1-M2 (along the horizontal axis). In the plot 320, the D1 electrode represents the common cathode electrode.

The remaining plots 321-327 show correlation of capture threshold between various other combinations of pacing vectors that utilize LV electrodes as associated common cathodes. The plot 321 shows the relation between capture thresholds exhibited by a number of patients for the D1-P4 pacing vector and the D1-RV coil pacing vector, where the D1 electrode represents the common cathode. Plot 322 correlates capture thresholds associated with the D1-P4 pacing vector and D1-M2 pacing vector, where the D1 electrode represents the common cathode. The plots 323-327 illustrate the following correlations: M2-P4 to M2-RV coil (where M2 is the common cathode); M3-M2 to M3-RV coil (where M3 is the common cathode); M3-P4 and M3-RV coil (where M3 is the common cathode); M3-P4 and M3-M2 (where M3 is the common cathode); and before—M2 and P4-RV coil (where P4 is the common cathode).

The plots 320-327 also include dividing lines 330-332 that separate each of the plots 320-327 into four equal zones based select ratios R of the capture thresholds. The ratio R=CAP1/CAP2, where CAP1 represents the capture threshold associated with the "secondary" pacing vector denoted along the vertical axis, while CAP2 represents the capture threshold associated with the "base" pacing vector denoted along the horizontal axis. The dividing lines 330-332 define zones where R>2; 2>=R>1; 1>=R>0.5; and 0.5>=R.

As illustrated in FIG. 3B, a substantial majority of the patients exhibited capture thresholds associated with the pacing vectors plotted along the vertical axis that fell within a factor of two (e.g. 2×) of the capture thresholds associated with the pacing vectors plotted along the horizontal axis. More specifically, over 95% of the patients exhibited capture thresholds associated with bipolar pacing configurations (both electrodes on a common lead) that were within 2× of the capture thresholds associated with unipolar pacing configurations (electrodes are not on the same lead). For example, with reference to the plot 320, approximately 1% of the patient population exhibited the capture threshold associated with the D1-M2 pacing vector that was greater than two times the capture threshold associated with the D1-RV coil pacing vector.

In the same plot 320, approximately 73% of the patients exhibited capture thresholds associated with the D1-M2 pacing vector that was between one and two times the capture threshold associated with the D1-RV coil pacing vector. An additional 35% of the patients exhibited a relation between the capture thresholds associated with the pair of pacing vectors where the ratio R was between 0.5 and 1.0, while approximate 1% of the patients exhibited a ratio between the capture thresholds of R less than 0.5. The remaining plots 321-327 also indicate the percentages of the patient population that exhibited a ratio of capture thresholds between the corresponding pacing vectors. For example, the plot 324 illustrates that 1%, 73%, 23% and 3% of the patient population fell within each of the corresponding zones, while the plot 326 illustrates that 6%, 23%, 70% and 1% of the patient population fell within each of the corresponding zones.

The data illustrated in FIG. 3B indicates that the capture thresholds associated with unipolar configurations are lower than the capture thresholds associated with bipolar configurations. The differences in the capture thresholds for unipolar configurations versus bipolar configurations that use a common cathode exhibit a somewhat predictable outer relation. For example, the outer relation in the data Illustrated in FIG. 3B represents a relationship of 2X (2 times).

FIG. 3C illustrates a series of histograms plotting differences between capture thresholds for the same patient data used to derive the graphs and plots in FIGS. 3A and 3B. The histograms 340-345 relate to different select combinations of electrodes and illustrate the differences between capture thresholds associated with bipolar pacing vectors and unipolar pacing vectors that utilize a common cathode. The histograms 340-345 illustrate differences in voltage along the horizontal axis and the number of patients that exhibit the corresponding voltage difference along the vertical axis.

More specifically, the histogram 340 illustrates in bar 350 that over 200 patients exhibited a difference between −0.25 V and 0.25 V in the capture thresholds associated with the D1-M2 electrode combination and the D1-RV coil electrode combination. The bar 352 illustrates that less than 100 patients exhibited a difference between 0.25 V and 0.75 V, while even fewer patients exhibited a difference below −0.25 V or greater than 0.75 V. In the histogram 343, the bar 353 illustrates that over 100 patients exhibited a difference between −0.25 V and 0.25 V between the capture thresholds associated with the M3-M2 electrode combination and M3-RV coil electric combinations. The bar 354 illustrates that approximately 100 patients exhibited a difference between 0.25 V and 0.75 V in connection with the capture thresholds associated with the M3-P4 electrode combination and M3-RV coil electrode combination. The remaining histograms 341-342 and 344-345 illustrate further relations between the differences in the corresponding electrode combinations.

From the histograms 340-345, various information can be derived. For example, a very high percentage of the patients exhibited bipolar capture thresholds within one volt above the unipolar capture threshold when the D1 electrode was used as a common cathode between related bipolar and unipolar configurations. In addition, more than 90% of the patients exhibited bipolar capture thresholds within 2 V above the unipolar capture threshold when the M2, M3 or P4 electrodes were used as the common cathode between related bipolar and unipolar configurations.

As explained herein, methods and systems are described that utilize the relationships illustrated in the plots and charts of FIGS. 3A-3C in connection with determining test ranges to use when searching for capture thresholds associated with various pacing vectors.

Figure 4A:
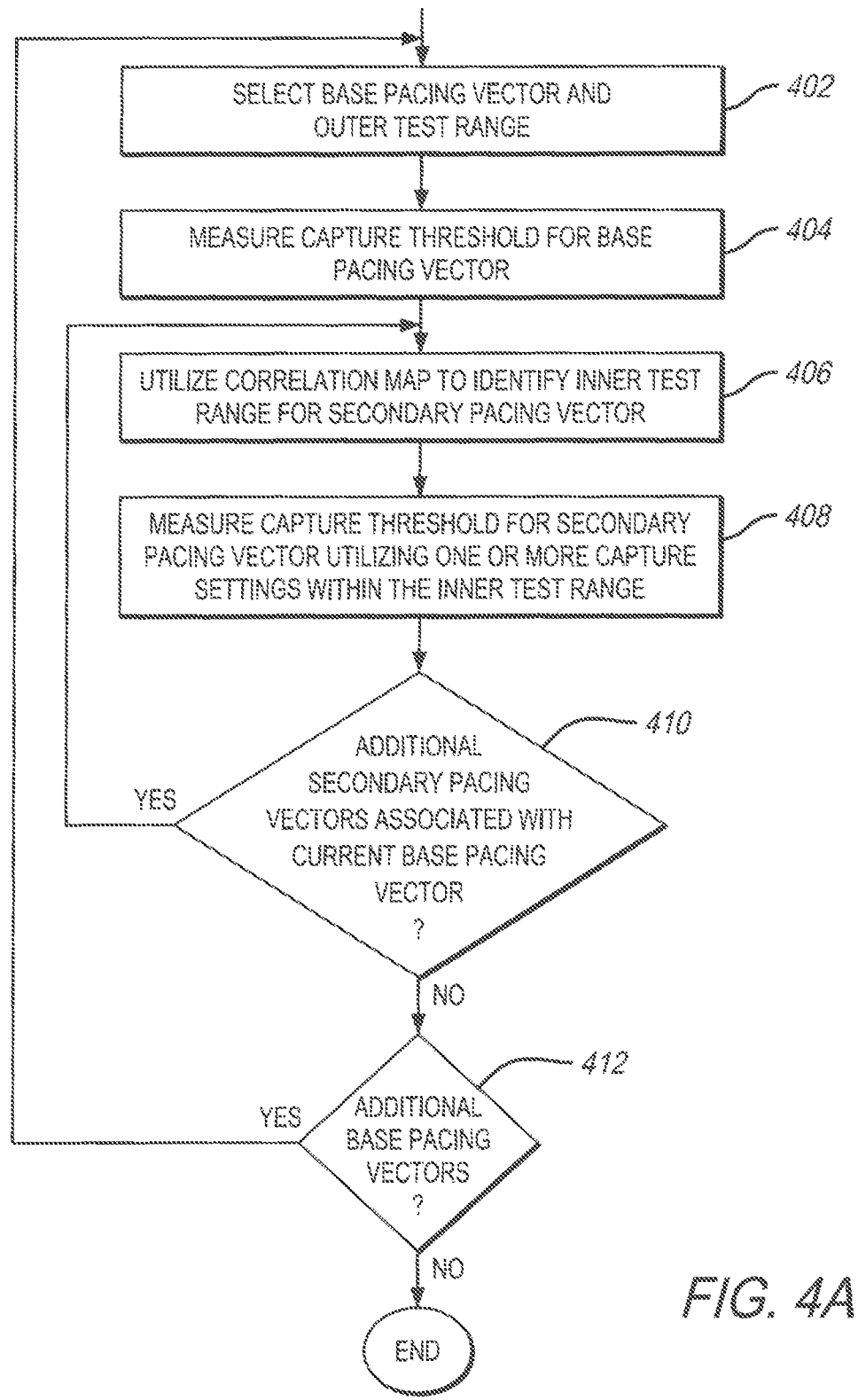
FIG. 4A illustrates a method for automatically determining capture thresholds for various pacing vectors in accordance with embodiments herein.

FIG. 4A illustrates a method for automatically determining capture thresholds for various pacing vectors in accordance with embodiments herein. At 402, the capture detection module 163 selects a base pacing vector and a base or outer test range. For example, the base pacing vector may be defined by a combination of electrodes that affords a unipolar configuration, such as the D1-RV coil electrode combination. When the D1-RV coil electrode combination is chosen, the RV coil electrode is set as an anode, while the D1 electrode is set as the cathode. The base or outer test range corresponds to upper and lower stimulation limits, and may be defined in various manners. The upper and lower stimulation limits correspond to a stimulation parameter related to an amount of stimulation amplitude that is delivered to the heart. For example, the stimulation limits may be defined based on voltage levels, in which case the upper and lower limits may represent predetermined upper and lower voltages (e.g. 7.5 V and zero).

Optionally, the stimulation limits may correspond to another parameter that defines stimulation pulses and stimulation amplitude, such as pulse width, a number of pulses, pulse shape and the like.

At 404, the capture detection module 163 performs one or more capture threshold measurements until identifying a capture threshold associated with the base pacing vector. For example, a base capture threshold is measured for a base pacing vector that is defined by a first LV electrode provided on the multi-pole LV lead and a second/reference electrode located remote from the LV chamber. For example, the second/reference electrode may represent an electrode in the RV, such as an RV tip electrode, RV coil electrode or RV ring electrodes. Optionally, the second/reference electrode may represent the CAN of the IMD. As another option, the second/reference electrode may be located in the right atrium and/or proximate to the left atrium. An example of operations that may be carried out at 404 are described below in more detail in connection with FIG. 4B. As explained below in connection with FIG. 4B, the measuring operation includes delivering a series of pacing pulses having different stimulation amplitudes that are varied over the outer test range, until losing capture.

At 406, the capture detection module 163 utilizes a correlation map to identify an inner or secondary test range for a secondary pacing vector. For example, the secondary pacing vector represents a vector that utilizes a cathode electrode that is common to the cathode electrode utilized in the base pacing vector. The secondary pacing vector also represents a vector that exhibits some level of correlation to the base pacing vector. For example, when the D1-RV coil electrode combination is used as the base pacing vector, the secondary pacing vector may be identified to be the D1-M2 electrode combination or the D1-P4 electrode combination (or another combination). The capture detection module 163 determines the secondary or inner test range by using the capture threshold measured at 404 as an input to the correlation map.

For example, one of the correlation maps illustrated in FIG. 2B may be used to Identify which combination of electrodes defines a secondary pacing vector known to have a relation with the present base pacing vector. The correlation maps from FIG. 2B may then also be used to identify one or more outer limits of an inner test range to be used when searching for the capture threshold associated with the secondary pacing vector. The correlation map may be defined in various manners and with varied levels of complexity. For example, the correlation map may represent a formula that defines the upper limit of the inner test range to be a factor of the capture threshold determined at 404 (e.g. 2*CAP1, where CAP1 represents the capture threshold measured at 404). As another example, the correlation map may add a predetermined fixed voltage to the capture threshold determined at 404 to obtain an upper limit of the inner test range (e.g., CAP1+2V). In the present example, the correlation map only defines the upper limit of the inner test range, while the lower limit of the inner test range remains the same as the lower limit of the outer test range.

Optionally, the correlation map may also define a lower limit for the inner test range that differs from the lower limit of the outer test range. As one example, the upper and lower limits of the inner test range may be defined as predetermined positive and negative multiples of the capture threshold determined at 404 (e.g. upper limit=CAP1*2 and lower limit=CAP1*(−1)). As another example, the upper and lower limits of the inner test range may be defined by adding and subtracting predetermined constants from the capture threshold determined at 404 (e.g. upper limit=CAP1+3V and lower limit=CAP1−2V).

Optionally, the correlation map may represent a linear function that maps an input (corresponding to the capture threshold of the base pacing vector) to an output (corresponding to the capture threshold of the secondary pacing vector). The linear function may have a nonzero slope such that, as the capture threshold for the base pacing vector increases, the output progressively increases to define higher upper limits for the secondary test range. Optionally, the correlation map may represent a non-linear function that maps inputs to outputs.

At 408, the capture detection module 163 measures the capture threshold for the secondary pacing vector utilizing one or more capture settings within the inner test range. An example of the operations that may be carried out at 408 are described below in more detail in connection with FIG. 4C. As explained below in connection with FIG. 4C, the measuring operation delivers a series of pacing pulses having different stimulation amplitudes that are varied over the inner test range, until capture is lost.

At 410, the process determines whether additional secondary pacing vectors exist that are associated with the current base pacing vector and are to be tested. If so, flow returns to 406. Otherwise, flow advances to 412. When the flow returns from 410 to 406, the operations of 406 and 408 are repeated for the next secondary pacing vector (and associated electrode combination).

At 412, the process determines whether additional base pacing vectors are to be tested. If so, flow returns to 402 and the operations at 402-410 are repeated. Otherwise, the process ends. With reference to the charts illustrated in FIGS. 3A-3C, the operations at 406 and 408 may be repeated for the secondary pacing vectors D1-M2 and D1-P4 electrode combinations utilizing corresponding inner test ranges as defined based on the capture threshold determined for the D1-RV coil electrode combination. Further, the operations at 402-412 may be repeated for multiple base pacing vectors, such as the D1-M2 electrode combination, the M2-RV coil electrode combination, the M3-RV coil electrode combination, the M3-M2 electrode combination and the P4-RV coil electrode combination.

Figure 4B:
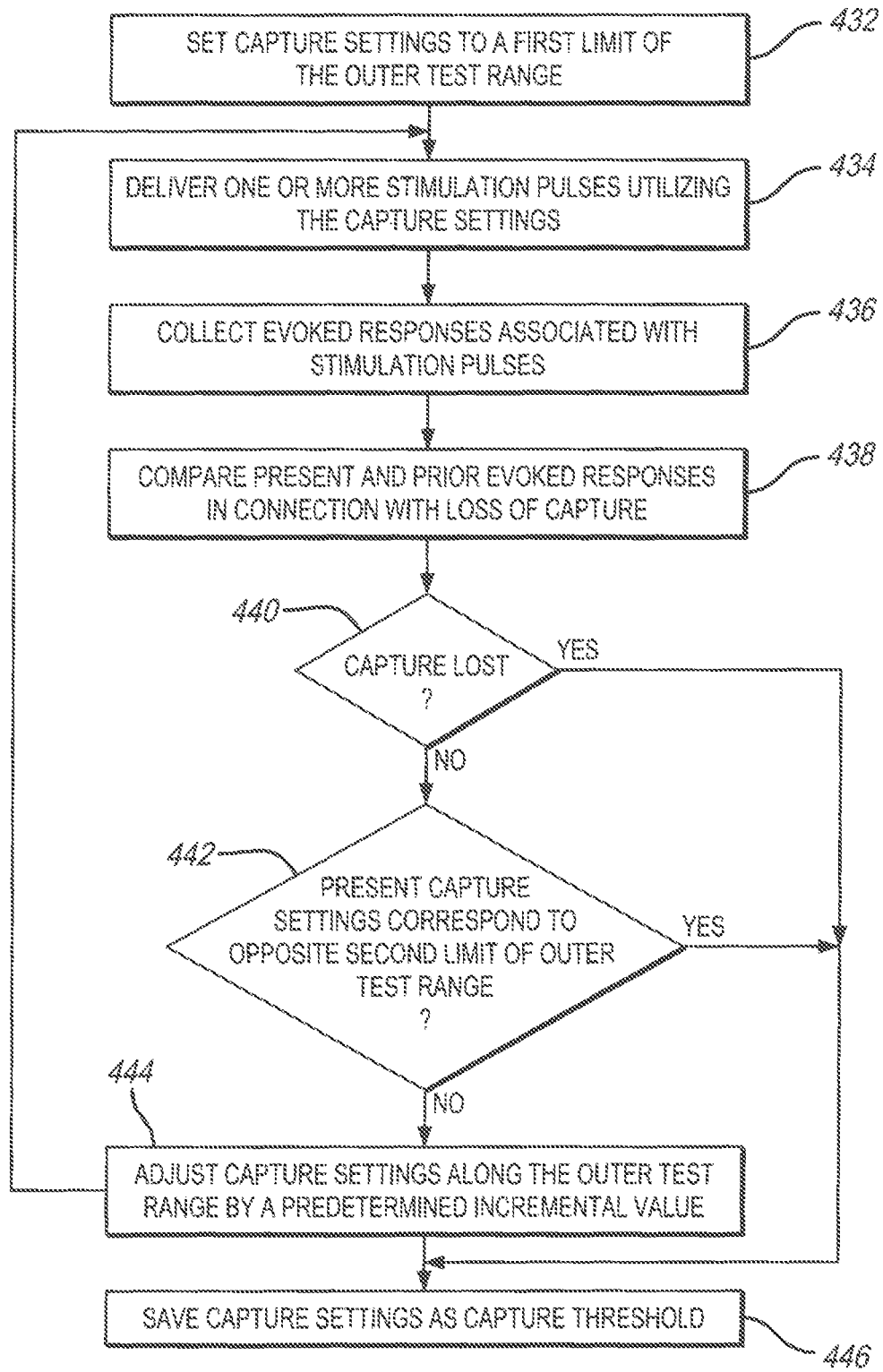
FIG. 4B illustrates an example of the operations performed to measure the capture threshold associated with a base pacing vector in accordance with embodiments herein.

FIG. 4B illustrates an example of the operations performed at 404 (FIG. 4A) to measure the capture threshold associated with a base pacing vector. Beginning at 432, the capture detection module 163 sets the stimulation parameters to a first limit of the outer test range. For example, when the parameter of interest corresponds to voltage, the initial stimulation pulse is set to deliver a pacing pulse with a relatively high pacing voltage (e.g. 7.5 V).

At 434, the capture detection module 163 delivers one or more stimulation pulses utilizing the stimulation parameters set at 432. At 436, the capture detection module 163 collects/senses evoke responses that occur in response to the delivered stimulation pulses. At 438, the capture detection module 163 analyzes the most recently collected evoke response to determine whether loss of capture has occurred. For example, the morphology or another characteristic of interest from the evoke response may be analyzed relative to one or more thresholds or templates. The threshold and template may be set to be representative of an evoke response that indicates that the stimulation pulse achieved capture of the heart tissue of Interest.

At 440, the capture detection module 163 determines whether capture has been lost based on the evoke response from the most recent stimulation pulse. When capture is lost, flow advances to 446. Otherwise, flow continues to 442. At 442, the capture detection module 163 determines whether the present stimulation limits correspond to an opposed second limit of the outer test range (e.g. the lowest stimulation voltage to be applied, the shortest stimulation pulse to be utilized, etc.). When a second limit is reached, flow moves from 442 to 446. Otherwise, flow continues to 444. At 444, the capture detection module 163 adjusts the capture settings associated with one or more stimulation parameters by a predetermined incremental value. For example, the voltage associated with the stimulation pulse may be decreased by a predetermined amount. Additionally or alternatively, the pulse width number of pulses and the like associated with the stimulation pulse may be decreased by a predetermined amount. Thereafter, flow returns to 434 and the operations at 434 through 442 are repeated.

In accordance with at least one embodiment, the operations of FIG. 4B are repeated, while measuring the base capture threshold, by delivering a series of stimulation pulses where successive stimulation pulses have different stimulation amplitudes starting at an upper limit of the outer test range and decreased by predetermined amounts.

The process of FIG. 4B is continuously repeated until either capture is lost for the heart tissue of interest or the process steps through the complete outer test range for the stimulation parameter of interest without losing capture. When either condition occurs, flow moves to 446 where the capture setting is saved as the capture threshold. For example, the capture threshold may represent the last stimulation voltage that successfully achieved capture or, when capture is never lost, the lowest stimulation voltage within the outer test range.

Figure 4C:
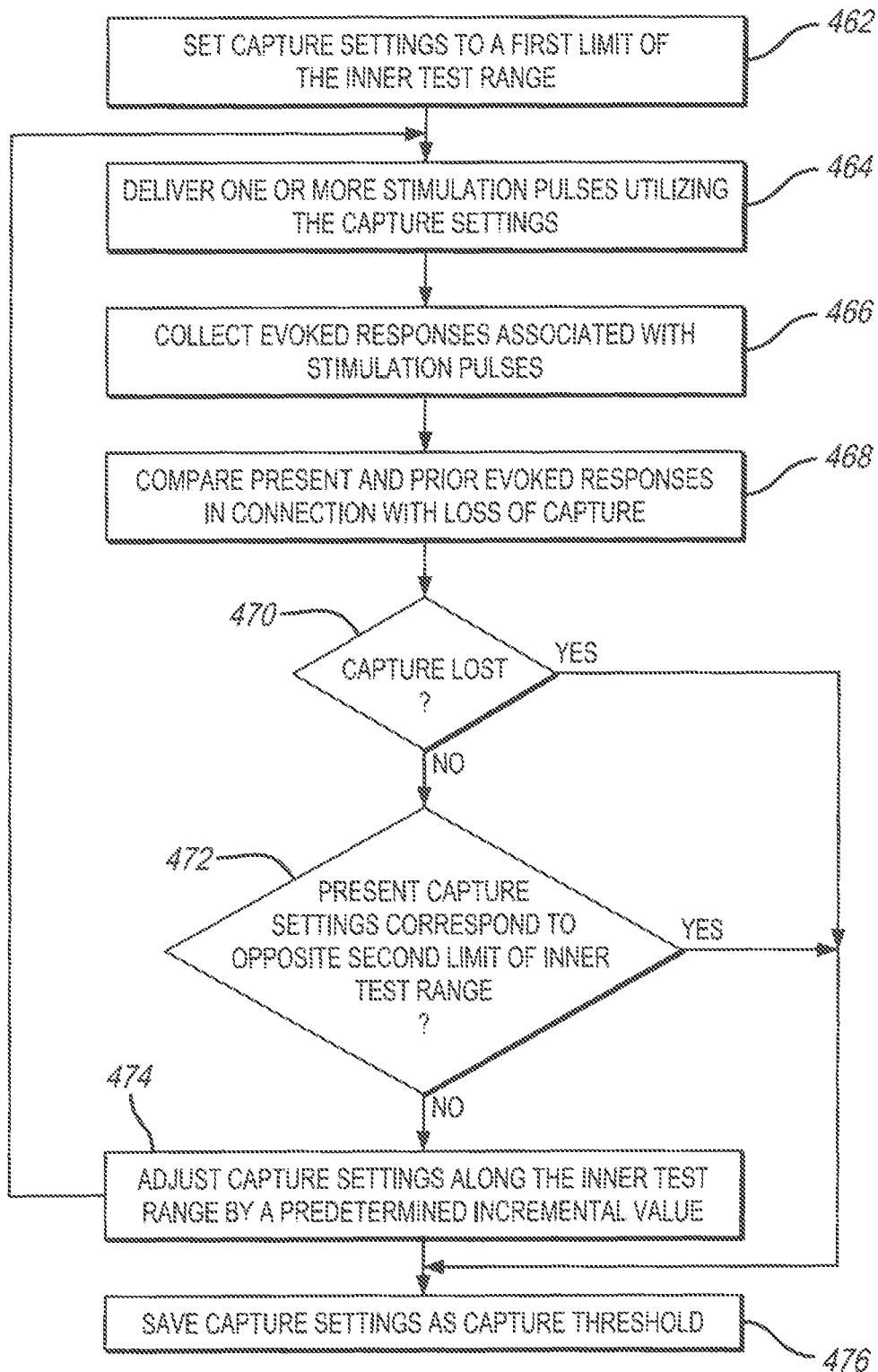
FIG. 4C illustrates an example of the operations performed to measure the capture threshold associated with a secondary pacing vector in accordance with embodiments herein.

FIG. 4C illustrates an example of the operations performed at 408 (FIG. 4A) to measure the capture threshold associated with a secondary pacing vector. Beginning at 462, the capture detection module 163 sets the stimulation parameters to a first limit of the inner test range. For example, when the parameter of interest corresponds to voltage, the initial stimulation pulses set to deliver a pacing pulls with a relatively high pacing voltage (e.g. 7.5 V).

At 464, the capture detection module 163 delivers one or more stimulation pulses utilizing the stimulation parameters set at 462. At 466, the capture detection module 163 collects evoke responses that occur in response to the stimulation pulses delivered. At 468, the capture detection module 163 analyzes the most recently collected evoke response to determine whether loss of capture has occurred. For example, the morphology or another characteristic of interest from the evoke response may be analyzed relative to one or more thresholds or templates. The threshold and templates may be set to be representative of evoke responses that indicate that the stimulation pulses achieved capture of the heart tissue of interest.

At 470, the capture detection module 163 determines whether capture has been lost based on the evoke response from the most recent stimulation pulse. When capture is lost, flow advances to 476. Otherwise, flow continues to 472. At 472, the capture detection module 163 determines whether the present stimulation limits correspond to an opposed second limit of the inner test range (e.g. the lowest stimulation voltage to be applied, the shortest stimulation pulse to be utilized, etc.). When a second limit is reached, flow moves from 472 to 476. Otherwise, flow continues to 474. At 474, the capture detection module 163 adjusts the capture settings associated with one or more stimulation parameters by a predetermined incremental value. For example, the voltage associated with the stimulation pulse may be decreased by a predetermined amount. Additionally or alternatively, the pulse width associated with the stimulation pulse may be decreased by a predetermined amount. Thereafter, flow returns to 464 and the operations at 464 through 472 are repeated.

The process of FIG. 4C is continuously repeated until either capture is lost for the part tissue of interest or the process steps through the complete inner test range for the stimulation parameter of interest without losing capture. When either condition occurs, flow moves to 476 where the capture setting is saved as the capture threshold. For example, the capture threshold may represent the last stimulation voltage that successfully achieved capture or, when capture is never lost, the lowest stimulation voltage within the inner test range.

Figure 4D:
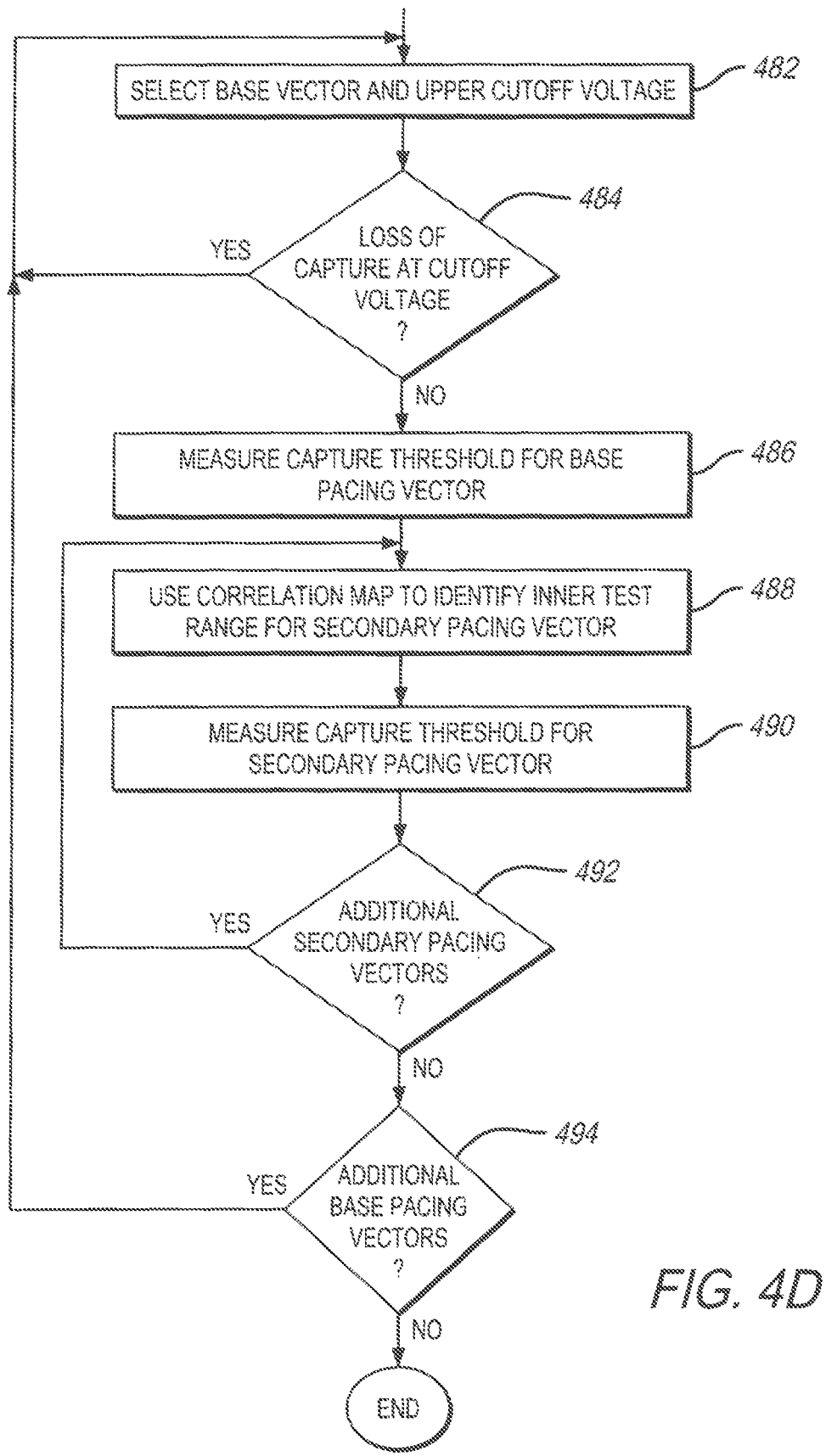
FIG. 4D illustrates a "quick scan" or "abbreviated scan" method for automatically determining capture thresholds for various pacing vectors in accordance with embodiments herein.

FIG. 4D illustrates a "quick scan" or "abbreviated scan" method for automatically determining capture thresholds for various pacing vectors in accordance with embodiments herein. For example, the quick scan method may limit the determination of capture thresholds to a subset of the available outer test range (e.g. utilizing an upper cut-off stimulation amplitude of 2 V or otherwise). As another example, the quick scan method may limit the determination of capture thresholds to a subset of the available inner test range. The quick scan method identifies vectors with thresholds below the cut-off in a relatively quick manner. For example, physicians may choose to only consider LV vectors with thresholds below a certain cut-off stimulation amplitude (e.g. 2 V). When a physician is interested only in a limited range of cut-off stimulation amplitudes, the capture threshold test described herein may be configured to immediately start with the desired cut-off stimulation amplitude. When loss of capture is detected at the desired cut-off stimulation amplitude, the process proceeds to the next base or secondary vector without determining the capture threshold associated with the present vector. When a capture threshold is detected, the process continues to decrement the test stimulation amplitude until loss of capture is determined. The quick scan method may be applied in connection with measuring the capture thresholds for base pacing vectors and/or for secondary pacing vectors.

At 482, the capture detection module 163 selects a base pacing vector and a base or outer test range having an abbreviated cut-off stimulation amplitude (e.g 2 V and the like). As explained herein, the base pacing vector may be defined by a combination of electrodes that affords a unipolar configuration, such as the D1-RV coil electrode combination. The base or outer test range corresponds to an abbreviated upper stimulation limit and a lower stimulation limits, which may be defined in various manners.

At 484, the capture detection module 163 determines whether loss of capture occurred at the cut-off stimulation amplitude. When loss of capture is detected, flow returns to 482 where a new base pacing vector is selected. When loss of capture occurs at the cut-off stimulation amplitude associated with a base pacing vector, during the abbreviated scan, no further capture threshold testing is performed in connection with the associated base pacing vector. Instead, the process moves on to one or more other base pacing vectors of potential interest.

Alternatively, at 484, when the capture detection module 163 determines that a capture threshold was measured at the cut-off stimulation amplitude, flow advances to 486. At 486, the capture detection module 163 performs one or more additional capture threshold measurements until identifying a capture threshold associated with the base pacing vector. An example of operations that may be carded out, at 484, are described in connection with FIG. 4B. The measuring operation includes delivering a series of pacing pulses having different stimulation amplitudes that are varied over the test range, until losing capture.

At 488, the capture detection module 163 utilizes a correlation map to identify an inner or secondary test range for a secondary pacing vector. For example, the secondary pacing vector represents a vector that utilizes a cathode electrode that is common to the cathode electrode utilized in the base pacing vector. The secondary pacing vector also represents a vector that exhibits some level of correlation to the base pacing vector. For example, one of the correlation maps illustrated in FIG. 2B may be used to identify which combination of electrodes defines a secondary pacing vector known to have a relation with the present base pacing vector.

At 490, the capture detection module 163 measures the capture threshold for the secondary pacing vector utilizing one or more capture settings within the inner test range. An example of the operations that may be carried out at 490 are described in more detail in connection with FIG. 4C. As explained below in connection with FIG. 4C, the measuring operation delivers a series of pacing pulses having different stimulation amplitudes that are varied over the inner test range, until capture is lost.

Optionally, at 490, the capture detection module 163 may perform an abbreviated capture threshold test in connection with the secondary pacing vector. For example, an initial capture threshold test may be applied at the secondary pacing vector utilizing the upper limit of the inner test range.

At 490, the capture detection module 163 may determine whether loss of capture occurred at the upper limit of the inner test range for the present secondary pacing vector. When loss of capture is detected, the present secondary pacing vector is not further tested for a capture threshold. Instead, flow advances to 492 and the present secondary pacing vector is disregarded.

At 492, the process determines whether additional secondary pacing vectors exist that are associated with the current base pacing vector and are to be tested. If so, flow returns to 488. Otherwise, flow advances to 494. When the flow returns from 492 to 488, the operations of 488 and 490 are repeated for the next secondary pacing vector. At 494, the process determines whether additional base pacing vectors are to be tested. If so, flow returns to 482 and the operations of FIG. 4D are repeated. Otherwise, the process ends.

Optionally, the abbreviated or quick scan process described in connection with FIG. 4D may be performed in connection with some or all base pacing vectors and/or only in connection with some or all secondary pacing vectors.

Figure 5:
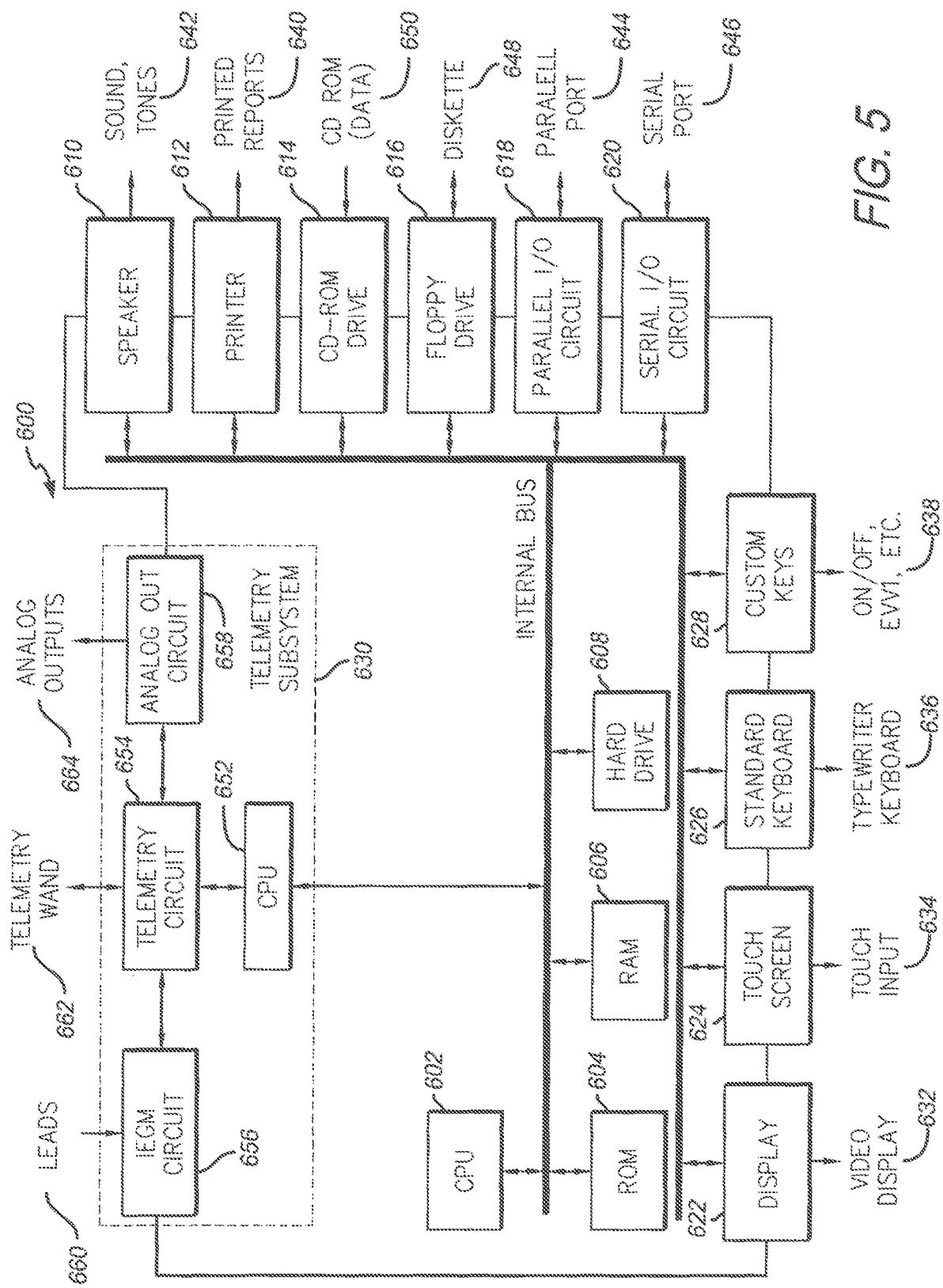
FIG. 5 illustrates a functional block diagram of an external device that is operated in accordance with the processes described herein.

FIG. 5 illustrates a functional block diagram of an external device 600 that is operated in accordance with the processes described herein and to interface with the implantable medical device 100 as shown in FIGS. 1 and 2 and described herein. The external device 600 may be the external programmer device 104 shown in FIG. 2. The external device 600 may take the form of a workstation, a portable computer, an IMD programmer, a PDA, a cell phone, and the like. The external device 600 includes an internal bus that connects/interfaces with a Central Processing Unit (CPU) 602, ROM 604, RAM 606, a hard drive 608, a speaker 610, a printer 612, a CD-ROM drive 614, a floppy drive 616, a parallel I/O circuit 618, a serial I/O circuit 620, a display 622, a touch screen 624, a standard keyboard 626, custom keys 628, and/or a telemetry subsystem 630. The internal bus is an address/data bus that transfers information between the various components described herein. The hard drive 608 may store operational programs as well as data, such as waveform templates, determinations on presence of PNS at various electrode locations, and/or capture thresholds for pacing vectors.

The CPU 602 includes a microprocessor, a micro-controller, and/or equivalent control circuitry, designed specifically to control interfacing with the external device 600 and with the IMD 100. The CPU 602 may include RAM or ROM memory, logic and timing circuitry, state machine circuitry, and/or I/O circuitry to interface with the IMD 100. The ROM 604, RAM 606 and/or hard drive 608 store program instructions that one executed by one or more processors (e.g., the CPU 602) to perform the operations described herein.

The display 622 may be connected to a video display 632. The display 622 displays various forms of information related to the processes described herein. The touch screen 624 may display graphic user information relating to the IMD 100. The touch screen 624 accepts a user's touch input 634 when selections are made. The keyboard 626 (e.g., a typewriter keyboard 636) allows a user to enter data to displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646.

The floppy drive 616 accepts diskettes 648. Optionally, the floppy drive 616 may include a USB port or other interface capable of communicating with a USB device such as a flash memory stick. The CD-ROM drive 614 accepts CD ROMs 650. The CD-ROM drive 614 optionally may include a DVD port capable of reading and/or writing DVDs.

The telemetry subsystem 630 includes a central processing unit (CPU) 652 in electrical communication with a telemetry circuit 654, which communicates with both an IEGM circuit 656 and an analog out circuit 658. The IEGM circuit 656 may be connected to leads 660. The IEGM circuit 656 is also connected to the implantable leads 120, 124 and 130 (shown in FIG. 1) to receive and process IEGM cardiac signals. Optionally, the IEGM cardiac signals sensed by the leads 120, 124 and 130 may be collected by the IMD 100 and then wirelessly transmitted to the telemetry subsystem 630 input of the external device 600.

The telemetry circuit 654 is connected to a telemetry wand 662. The analog out circuit 658 includes communication circuits to communicate with analog outputs 664. The external device 600 may wirelessly communicate with the IMD 100 and utilize protocols, such as Bluetooth, GSM, infrared wireless LANs, HIPERLAN, 3G, 4G, satellite, as well as circuit and packet data protocols, and the like. Alternatively, a hard-wired connection may be used to connect the external device 600 to the IMD 100.

CLOSING

The block diagrams of embodiments herein illustrate various blocks that may be labeled "module", "unit" and the like. It is to be understood that the modules, units, etc. represent circuits that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard-wired to perform the functions described herein. Optionally, the hardware may include electronic circuits that include and/or are connected to one or more logic-based devices, such as microprocessors, processors, controllers, or the like. Optionally, the modules, units, etc. may represent processing circuitry such as one or more field programmable gate array (FPGA), application specific integrated circuit (ASIC), or microprocessor. The modules, units, etc. in various embodiments may be configured to execute one or more algorithms to perform functions described herein. The one or more algorithms may include aspects of embodiments disclosed herein, whether or not expressly Identified in a flowchart or a method.

The various methods as illustrated in the FIGS and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of Information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are Intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A system for automatically determining capture thresholds for an implantable medical device adapted to deliver cardiac stimulus pacing using a multi-pole left ventricular (L V) lead. comprising:
   at least one processor;
   a pulse generator coupled to the multi-pole L V lead, the pulse generator being adapted to deliver to deliver cardiac stimulus pacing to one or more electrode of the multi-pole LV lead; and
   a memory coupled to the at least one processor, wherein the memory stores program instructions, wherein the program instructions are executable by the at least one processor to:
   measure a base capture threshold for a base pacing vector utilizing stimulation pulses delivered by the pulse generator varied over at least a portion of an outer capture threshold test range, the base pacing vector defined by a first LV electrode provided on the LV lead and a secondary electrode located remote from an LV chamber;
   designate a secondary pacing vector that includes the first LV electrode and a second LV electrode provided on the LV lead;
   define an inner test range having limits based on the base capture threshold, wherein at least one of the limits for the inner test range differs from a corresponding limit for the outer test range; and
   measure a secondary capture threshold associated with the secondary pacing vector utilizing stimulation pulses varied over at least a portion of the inner test range.

2. The system of claim 1, further comprising a pulse generator that delivers, in connection with measuring the base capture threshold, successive stimulation pulses that have different stimulation amplitudes starting at an upper limit of the outer test range and decreasing by predetermined amounts.

3. The system of claim 1, further comprising a pulse generator that delivers, in connection with measuring the secondary capture threshold, one or more pacing pulses having stimulation amplitudes varying over the inner test range.

4. The system of claim 3, wherein the pulse generator delivers one or more pacing pulses beginning with an initial stimulation amplitude having a voltage that is lower than a voltage of an initial stimulation amplitude associated with the outer test range used to measure the base capture threshold.

5. The system of claim 3, wherein the pulse generator, in connection with measuring the base and secondary capture thresholds, begins at first and second outer voltages corresponding to one of the limits of the outer and inner test ranges, respectively, the first and second outer voltages differing from one another.

6. The system of claim 1, further comprising a correlation map defining a relation between the base capture threshold and at least one outer limit of the inner test range.

7. The system of claim 1, wherein the second outer voltage is set to equal a predetermined multiple of the first outer voltage or to equal a difference between the first outer voltage and a predetermined offset.

8. The system of claim 1, further comprising a pulse generator and a switch, the switch defining the base and secondary pacing vectors by connecting the pulse generator to the first LV electrode in a manner that sets the first LV electrode as a cathode electrode, the switch connecting the second electrode and the neighbor LV electrode as anode electrodes.

9. The system of claim 1, further comprising a switch that sets the base pacing vector to represent a unipolar pacing configuration and that sets the secondary pacing vector to represent a bipolar pacing configuration.

* * * * *